United States Patent
Yue et al.

(10) Patent No.: US 12,343,110 B2
(45) Date of Patent: Jul. 1, 2025

(54) MULTI-MODAL IMAGING DEVICE

(71) Applicants: BEIHANG UNIVERSITY, Beijing (CN); SUZHOU SURGI-MASTER HIGH TECH CO., LTD., Jiangsu (CN)

(72) Inventors: Shuhua Yue, Beijing (CN); Xun Chen, Beijing (CN); Pu Wang, Beijing (CN)

(73) Assignees: BEIHANG UNIVERSITY, Beijing (CN); SUZHOU SURGI-MASTER HIGH TECH CO., LTD., Jiangsu (CN)

( * ) Notice: Subject to any disclaimer, the term of this patent is extended or adjusted under 35 U.S.C. 154(b) by 0 days.

(21) Appl. No.: 18/670,811

(22) Filed: May 22, 2024

(65) Prior Publication Data

US 2024/0306913 A1 Sep. 19, 2024

Related U.S. Application Data

(63) Continuation of application No. PCT/CN2022/129956, filed on Nov. 4, 2022.

(30) Foreign Application Priority Data

Nov. 22, 2021 (CN) .......................... 202111381679.X

(51) Int. Cl.
A61B 5/00 (2006.01)
(52) U.S. Cl.
CPC .......... *A61B 5/0035* (2013.01); *A61B 5/0066* (2013.01); *A61B 5/0075* (2013.01);
(Continued)
(58) Field of Classification Search
CPC ................................................... A61B 5/0035
See application file for complete search history.

(56) References Cited

U.S. PATENT DOCUMENTS

2004/0254474 A1 12/2004 Seibel et al.
2005/0283058 A1 12/2005 Choo-Smith et al.
(Continued)

FOREIGN PATENT DOCUMENTS

CN 112089404 A 12/2012
CN 112930470 A 6/2021
(Continued)

OTHER PUBLICATIONS

International Search Report for corresponding International Patent Application No. PCT/CN2022/129956, mailed Jan. 18, 2023, 7 pages.

*Primary Examiner* — Joseph M Santos Rodriguez
(74) *Attorney, Agent, or Firm* — Cooper Legal Group, LLC

(57) ABSTRACT

The present disclosure relates to a multi-modal imaging device. The multi-modal imaging device includes: a Raman spectroscopic analysis module configured to obtain Raman spectroscopic information of a target object on a first sampling position by using excitation light; an optical coherence tomography module configured to obtain a tissue structure image of the target object on a second sampling position by using imaging detection light; and a co-localization module configured to control the first sampling position of the excitation light in the Raman spectroscopic analysis module and/or the second sampling position in the optical coherence tomography module according to a determined concerned area of the target object, so that the first sampling position and the second sampling position are spatially co-localized in the concerned area.

20 Claims, 5 Drawing Sheets

(52) U.S. Cl.
CPC .......... *A61B 5/0084* (2013.01); *A61B 5/6847* (2013.01); *A61B 2560/0462* (2013.01); *A61B 2562/0233* (2013.01); *A61B 2576/00* (2013.01)

(56) References Cited

U.S. PATENT DOCUMENTS

| | | |
|---|---|---|
| 2007/0213618 A1 | 9/2007 | Li et al. |
| 2009/0021724 A1 | 1/2009 | Mahadevan-Jansen et al. |
| 2010/0315632 A1 | 12/2010 | Brennan, III |
| 2012/0188538 A1 | 7/2012 | Patil et al. |
| 2020/0000341 A1 | 1/2020 | Messerschmidt et al. |
| 2020/0110258 A1 | 4/2020 | Swanson |

FOREIGN PATENT DOCUMENTS

| | | |
|---|---|---|
| CN | 113812928 A | 12/2021 |
| CN | 113812929 A | 12/2021 |
| CN | 114795120 A | 7/2022 |
| WO | 2018217171 A1 | 11/2018 |
| WO | 2021113949 A1 | 6/2021 |

MULTI-MODAL IMAGING DEVICE

CROSS-REFERENCE TO RELATED APPLICATION

This application is a continuation of PCT application No. PCT/CN2022/129956, filed on Nov. 4, 2022, which claims the priority and benefit of Chinese patent application No. 202111381679.X, filed on Nov. 22, 2021. The entireties of PCT application No. PCT/CN2022/129956 and Chinese patent application No. 202111381679.X are hereby incorporated by reference herein and made a part of this specification.

TECHNICAL FIELD

The present disclosure relates to an optical imaging device for test or diagnosis, in particular to a multi-modal imaging device, in more particular to a multi-modal endoscope based on Raman spectroscopy and optical coherence tomography.

BACKGROUND

Early screening and test for cancers and postoperative reexamination are important means to improve a survival rate of patients, while endoscope imaging devices are important image diagnosis means for early screening and test for cancers and postoperative reexamination.

Optical coherence tomography (also known as optical coherent imaging, abbreviated as OCT), is an observation means for scattering light coherence imaging for physiological tissues. Optical coherence tomography has high spatial resolution, e.g., about 10 μm, which allows real-time non-invasive test for tissue scattering changes, provides two-dimensional or three-dimensional micrometer-scale tissue structures/morphological information, and achieves visual infiltration imaging. However, when used for early diagnosis for cancers, optical coherence tomography is not high in accuracy. For example, the sensitivity and specificity of optical coherence tomography for diagnosis of cervical intraepithelial neoplasia are only 88% and 69%.

Raman spectroscopy is an analysis means for obtaining information on aspects such as vibration and rotation of molecules by utilizing a Raman scattering effect of the molecules. Raman spectroscopy is related to molecular chemical bond information, and can recognize different types of molecules and evaluate relative concentration peaks according to different intensities. The accuracy and specificity of Raman spectroscopy for tumor diagnosis are higher than other methods. For example, the sensitivity of Raman spectroscopy for diagnosis of cervical intraepithelial neoplasia (CIN) is 93.5%, and the specificity is 97.8%; the sensitivity and specificity of Raman spectroscopy for diagnosis of early glioma are as high as 93% and 91%, respectively; and comparatively, the sensitivity and specificity of nuclear magnetic resonance diagnosis are only 88% and 54%, respectively. However, a Raman spectroscopic endoscope cannot provide a wide field-of-view imaging mode of a white light endoscope or a narrow-band endoscope and an optical coherence tomography, autofluorescence or confocal endoscope so as to be incapable of visually monitoring suspicious lesion areas during endoscopy.

Therefore, in order to improve the efficiency and accuracy of diagnosis/screening, it is expected that, on one hand, tissue structure image information (optical coherence tomographic information) can be obtained, and on the other hand, molecular structure information (Raman spectroscopic information) with high diagnosis sensitivity and specificity can also be obtained. However, it is still not enough for diagnosis and screening to only obtain the two aspects of information due to a fact that the two aspects of information can be combined together to provide meaningful auxiliary information for diagnosis/screening of cancers/tumors only when the two aspects of information are from the same spatially co-localized area (that is, the two aspects of information are from the basically same spatial position). If the two aspects of information are from spatially-biased positions, that is, the above-mentioned two aspects of information are respectively from spatially unmatched (non-co-localized) areas, the two aspects of information represents different information of different areas (although the different areas may partially overlap), respectively. At the moment, it is not appropriate to combine the two aspects due to a fact that such a combination lowers the accuracy of spatial information, which is contrary to a goal mentioned as above that the two aspects of information is expected to be combined to improve the accuracy.

Thus, it can be seen that the tissue structure image information and the Raman spectroscopic information which are spatially co-localized need to be obtained. The higher the spatial co-localization degree of the two aspects of information is, the more beneficial to the combination of the two aspects of information, thereby improving the accuracy and efficiency of diagnosis/screening.

Besides, since a speed (such as higher than 100 frames/second) of optical coherence tomography is not matched with a speed (2-5 Hz) of Raman spectroscopy test, they cannot be combined together at a high efficiency. Obviously, due to the low speed of the Raman spectroscopy test, even if optical coherence tomography is combined with the Raman spectroscopy test, it still takes a relatively long time to obtain comprehensive information. Therefore, it is also expected to obtain tissue structure image information and Raman spectroscopic information at a higher speed. For example, optical coherence tomography and Raman spectroscopy operate in a cooperative mode so as to improve the efficiency, accuracy and specificity of cancer screening.

Finally, it is also expected that a size of a probe of such a device is small enough (such as at least smaller than 10 mm) so as to be integrated with an existing endoscope system (such as a white light endoscope or a narrow-band endoscope).

SUMMARY

For solving the above-mentioned problems, the present disclosure provides a multi-modal imaging device. The multi-modal imaging device in the present disclosure includes a Raman spectroscopic analysis module, an optical coherence tomography module, and a co-localization module. According to the multi-modal imaging device in the present disclosure, the Raman spectroscopic analysis module and the optical coherence tomography module achieve imaging and test for a target object in the same co-localized area by using the co-localization module. Besides, the Raman spectroscopic analysis module and the optical coherence tomography module of the multi-modal imaging device in the present disclosure cooperatively operate, thereby obtaining a diagnosis basis required for cancer screening at high efficiency, high accuracy and high specificity. Due to the design of the multi-modal imaging device in the present disclosure, a probe is also allowed to be produced with a smaller size, which is beneficial to integration into an existing endoscope system.

An embodiment of the present disclosure provides a multi-modal imaging device, including:
- a Raman spectroscopic analysis module configured to obtain Raman spectroscopic information of a target object on a first sampling position by using excitation light;
- an optical coherence tomography module configured to obtain a tissue structure image of the target object on a second sampling position by using imaging detection light; and
- a co-localization module configured to control the first sampling position of the excitation light in the Raman spectroscopic analysis module and/or the second sampling position in the optical coherence tomography module according to a determined concerned area of the target object, so that the first sampling position and the second sampling position are spatially co-localized in the concerned area.

Optionally, the multi-modal imaging device includes a probe provided with a shell and a detection window and configured to detect the target object, and the excitation light from the Raman spectroscopic analysis module and the imaging detection light from the optical coherence tomography module are coupled in the probe.

Optionally, the Raman spectroscopic analysis module includes a first light source, a
first beam splitting mirror, a first coupling objective lens, a first optical fiber, a spectrometer, a first lens group, and a first dichroscope; and
the first beam splitting mirror is configured to transmit excitation light from the first light source and reflect Raman spectroscopy scattering signal light from the target object, the spectrometer is configured to receive the Raman spectroscopy scattering signal light from the target object reflected by the first beam splitting mirror, the first coupling objective lens is configured to receive emergent light from the first beam splitting mirror or the co-localization module, the first optical fiber is configured to receive emergent light from the first coupling objective lens, the first lens group is configured to receive emergent light from the first optical fiber, and the first dichroscope is configured to receive and transmit emergent light from the first lens group.

Optionally, a grating and a receiving lens are arranged between the spectrometer and the first beam splitting mirror, the grating is configured to split reflected light from the first beam splitting mirror, the receiving lens is configured to receive emergent light from the grating, and the spectrometer is configured to receive emergent light from the receiving lens.

Optionally, the first lens group includes a collective lens.

Optionally, the first optical fiber includes a multi-core optical fiber, wherein a central fiber core group consisting of at least one fiber core on a central part of the multi-core optical fiber is configured to transmit Raman spectroscopy excitation light from the first light source, and a plurality of peripheral fiber core groups of groups consisting of at least one fiber core surrounding the central part in the multi-core optical fiber are configured to transmit the Raman spectroscopy scattering signal light.

Optionally, the peripheral fiber core groups are symmetrically distributed with the central fiber core group as a center.

Optionally, a band-pass fiber is arranged on a tail end of a side, close to the target object, of the central fiber core group, and notch fibers and/or long-pass filters are arranged on tail ends of sides, close to the target object, of the peripheral fiber core groups.

Optionally, cross sections of the central fiber core group and the peripheral fiber core groups are basically round.

Optionally, the optical coherence tomography module includes a second light source, a beam splitter, an interferometer, a second optical fiber, a scanning sub-module, a detector, a second lens group, and a reflecting mirror;
the second light source, the interferometer, the detector and the scanning sub-module are optically coupled to the beam splitter; the scanning sub-module is optically coupled to the beam splitter via the second optical fiber; one part of the second optical fiber passes through the scanning sub-module; and
the second lens group is configured to receive emergent light from the second optical fiber, the reflecting mirror is configured to reflect emergent light from the second lens group, and the first dichroscope is configured to reflect reflected light from the reflecting mirror, so that light from the first lens group is coupled with light from the second lens group.

Optionally, the second light source and/or the interferometer and/or the detector are optically coupled to the beam splitter via a coupling optical fiber.

Optionally, the first lens group and the second lens group are arranged in parallel in the probe, and the first dichroscope, the scanning sub-module, the reflecting mirror and at least one part of the second optical fiber are arranged in the probe.

Optionally, the scanning sub-module is configured to control imaging detection light from the second light source by controlling the position of the second optical fiber so as to obtain a position of the tissue structure image of the target object.

Optionally, the scanning sub-module includes a piezoelectric ceramic tube.

Optionally, the second lens group includes a second focusing lens and a diffraction lens, and the diffraction lens is arranged between the second focusing lens and the reflecting mirror.

Optionally, a circulator is arranged between the detector and the beam splitter.

Optionally, the second optical fiber and/or the coupling optical fiber includes a single-mode optical fiber.

Optionally, the co-localization module is arranged in an incident light path of the excitation light from the Raman spectroscopic analysis module.

Optionally, the co-localization module is arranged between the first beam splitting mirror and the first coupling objective lens.

Optionally, the co-localization module has a first mode and a second mode which are switchable;
in the first mode, the co-localization module does not change the first sampling position; and
in the second mode, the co-localization module is configured to control the first sampling position.

Optionally, the co-localization module includes a first flip mirror, a second flip mirror, a first scanning galvanometer, and a second scanning galvanometer; the first flip mirror and the second flip mirror are arranged between the first beam splitting mirror and the first coupling objective lens;
the first flip mirror and the second flip mirror are configured to control mirror surfaces of the first flip mirror and the second flip mirror to be parallel or not parallel to a light path between the first beam splitting mirror and the first coupling objective lens by rotating around an axis orthogonal to the light path between the first beam splitting mirror and the first coupling objective lens; and the first scanning galvanometer and the second scanning galvanometer are configured to control the first sampling position by rotating around different axes;

wherein in the first mode, the mirror surfaces of the first flip mirror and the second flip mirror are parallel to the light path between the first beam splitting mirror and the first coupling objective lens; and in the second mode, the mirror surfaces of the first flip mirror and the second flip mirror are not parallel to the light path between the first beam splitting mirror and the first coupling objective lens.

Optionally, in the second mode, the first flip mirror is configured to receive and reflect light transmitted by the first beam splitting mirror, the first scanning galvanometer is configured to receive and reflect reflected light from the first flip mirror, the second scanning galvanometer is configured to receive and reflect reflected light from the first scanning galvanometer, the second flip mirror is configured to receive and reflect reflected light from the second scanning galvanometer, and the first coupling objective lens is configured to receive reflected light from the second flip mirror.

Optionally, each of the first scanning galvanometer and the second scanning galvanometer includes a Galvo galvanometer, an MEMS-driven reflecting mirror or a resonant galvanometer.

Optionally, the multi-modal imaging device in an embodiment of the present disclosure further includes: a detection lens and a detection optical fiber;

the Raman spectroscopic analysis module further includes a second dichroscope;

the optical coherence tomography module includes a second light source, a beam splitter, an interferometer, a remote scanning sub-module, and a detector;

wherein the first beam splitting mirror, the co-localization module, the second dichroscope and the first coupling objective lens are sequentially arranged in a transmission direction of emergent light from the first light source;

the second dichroscope is configured to transmit emergent light from the co-localization module or emergent light from the first beam splitting mirror and reflect the imaging detection light from the second light source, so that the emergent light is coupled with the imaging detection light;

the first coupling objective lens is configured to receive coupled light from the second dichroscope;

the detection optical fiber is configured to receive emergent light from the first coupling objective lens;

the detection lens is configured to receive emergent light from the detection optical fiber;

the remote scanning sub-module is arranged between the second dichroscope and the beam splitter and is configured to receive and reflect the imaging detection light from the second light source and transmitted by the beam splitter; and the second light source, the interferometer and the detector are optically coupled to the beam splitter.

Optionally, the second light source and/or the interferometer and/or the detector are optically coupled to the beam splitter by the coupling optical fiber.

Optionally, the multi-modal imaging device includes a probe, and the detection lens and at least one part of the detection optical fiber are arranged in the probe.

Optionally, the co-localization module has a first mode and a second mode which are switchable;

in the first mode, the co-localization module does not change the first sampling position; and in the second mode, the co-localization module is configured to control the first sampling position.

Optionally, the co-localization module includes a first flip mirror, a second flip mirror, a first scanning galvanometer, and a second scanning galvanometer; the first flip mirror and the second flip mirror are arranged between the first beam splitting mirror and the second dichroscope;

the first flip mirror and the second flip mirror are configured to control mirror surfaces of the first flip mirror and the second flip mirror to be parallel or not parallel to a light path between the first beam splitting mirror and the second dichroscope by rotating around an axis orthogonal to the light path between the first beam splitting mirror and the second dichroscope; and the first scanning galvanometer and the second scanning galvanometer are configured to control the first sampling position by rotating around different axes;

wherein in the first mode, the mirror surfaces of the first flip mirror and the second flip mirror are parallel to the light path between the first beam splitting mirror and the second dichroscope; and in the second mode, the mirror surfaces of the first flip mirror and the second flip mirror are not parallel to the light path between the first beam splitting mirror and the second dichroscope.

Optionally, in the second mode, the first flip mirror is configured to receive and reflect light transmitted by the first beam splitting mirror, the first scanning galvanometer is configured to receive and reflect reflected light from the first flip mirror, the second scanning galvanometer is configured to receive and reflect reflected light from the first scanning galvanometer, the second flip mirror is configured to receive and reflect reflected light from the second scanning galvanometer, and the second dichroscope is configured to receive and transmit reflected light from the second flip mirror.

Optionally, each of the first scanning galvanometer and the second scanning galvanometer includes a Galvo galvanometer, an MEMS-driven reflecting mirror or a resonant galvanometer.

Optionally, the remote scanning sub-module is configured to control imaging detection light from the second light source by rotating around at least two axes so as to obtain a position of the tissue structure image of the target object.

Optionally, the detection optical fiber includes a multi-core optical fiber, a central fiber core group consisting of at least one fiber core on a central part of the multi-core optical fiber is configured to transmit the imaging detection light from the second light source and light from the target object and configured to obtain the tissue structure image of the target object, a plurality of peripheral fiber core groups of groups consisting of at least one fiber core surrounding the central part in the multi-core optical fiber are respectively configured to transmit Raman spectroscopy excitation light and Raman spectroscopy scattering signal light from the first light source.

Optionally, the peripheral fiber core groups configured to transmit the Raman spectroscopy excitation light and the peripheral fiber core groups configured to transmit the Raman spectroscopy scattering signal light in the multi-modal imaging device are arranged alternatively.

Optionally, band-pass fibers are arranged on tail ends of sides, close to the target object, of the central fiber core group and the peripheral fiber core groups configured to transmit the Raman spectroscopy excitation light, and notch fibers and/or long-pass filters are arranged on tail ends of sides, close to the target object, of the peripheral fiber core groups configured to transmit the Raman spectroscopy scattering signal light.

Optionally, cross sections of the central fiber core group and the peripheral fiber core groups are basically round.

Optionally, the cross sectional area of the central fiber core group is greater than the cross sectional area of single peripheral fiber core group configured to transmit the Raman spectroscopy excitation light and the cross sectional area of single peripheral fiber core group configured to transmit the Raman spectroscopy scattering signal light.

Optionally, the remote scanning sub-module includes a remote scanning galvanometer.

Optionally, the remote scanning galvanometer includes an MEMS-driven reflecting mirror, a Galvo galvanometer or a resonant galvanometer.

Optionally, the detection lens includes a detection focusing lens.

Optionally, a grating and a receiving lens are arranged between the spectrometer and the first beam splitting mirror, the grating is configured to split reflected light from the first beam splitting mirror, the receiving lens is configured to receive emergent light from the grating, and the spectrometer is configured to receive emergent light from the receiving lens.

Optionally, the first light source and the second light source are respectively provided with a first light source switch and a second light source switch, and an optional middle reflecting mirror configured to reflect the excitation light from the first light source to the first beam splitting mirror is arranged between the first light source and the first beam splitting mirror.

Optionally, the co-localization module is configured to move the first sampling position to basically overlap with a position of the concerned area.

Optionally, the first lens group is configured to enable a size of a light spot of the excitation light from the Raman spectroscopic analysis module on the first sampling position is basically the same as a size of the concerned area.

Optionally, the co-localization module is configured to move the first sampling position to a position basically overlapping with the concerned area.

Optionally, the co-localization module is configured to synchronously control the first sampling position and the second sampling position with the remote scanning sub-module, so that the first sampling position basically overlaps with the second sampling position.

Optionally, the multi-modal imaging device in the present disclosure further includes:
- an image processing module configured to fuse the Raman spectroscopic information of the first sampling position and the tissue structure image of the second sampling position, which are spatially co-localized, so as to generate fused multi-modal information of the concerned area.

Optionally, the multi-modal imaging device in the present disclosure is an endoscope.

Optionally, a diameter of the probe of the multi-modal imaging device in the present disclosure is 2-10 mm.

Optionally, a diameter of the probe of the multi-modal imaging device in the present disclosure is 2-5 mm.

Optionally, the concerned area of the target object is determined from the image of the target object, which is acquired by an imaging device different from the multi-modal imaging device, the spectroscopic information acquired by the Raman spectroscopic analysis module or the image acquired by the optical coherence tomography module.

Optionally, the imaging device different from the multi-modal imaging device includes a white light endoscope module and/or a narrow-band imaging module.

Optionally, the concerned area is a medical concerned area.

According to the multi-modal imaging device in the present disclosure, the Raman spectroscopic analysis module and the optical coherence tomography module can detect/test the same area by using the co-localization module so as to obtain the tissue structure image and the Raman spectroscopic information which are spatially co-localized.

In addition, according to the multi-modal imaging device in the present disclosure, the Raman spectroscopic analysis module and the optical coherence tomography module can also cooperatively operate in a high-efficiency mode by using the co-localization module. Therefore, during the diagnosis of cancers, the advantages of the accuracy and specificity of the Raman spectroscopic analysis module and the advantage that the optical coherence tomography module two-dimensionally or three-dimensionally obtains the tissue structure information with a high spatial resolution can be used at the same time, and at the same time, the problem that the speed of Raman spectroscopy test is lower than the speed of optical coherence tomography is avoided. In such a case, spatial co-localization of Raman spectroscopic analysis and optical coherence tomography is also achieved.

Finally, the probe in the present disclosure can be smaller in size. Especially, the above-mentioned probe in another implementation of an embodiment of the present disclosure can even have a small size of 2-5 mm, which allows the imaging device in the present disclosure to be easily integrated into the existing endoscope system.

BRIEF DESCRIPTION OF THE DRAWINGS

To describe the technical solutions in the embodiments of the present disclosure more clearly, the accompanying drawings required for describing the embodiments will be briefly introduced below. Apparently, the accompanying drawings in the following description show only some exemplary embodiments of the present disclosure, and those of ordinary skill in the art may still derive other accompanying drawings from these accompanying drawings without creative efforts.

LIST OF REFERENCE SIGNS

Figure 1:
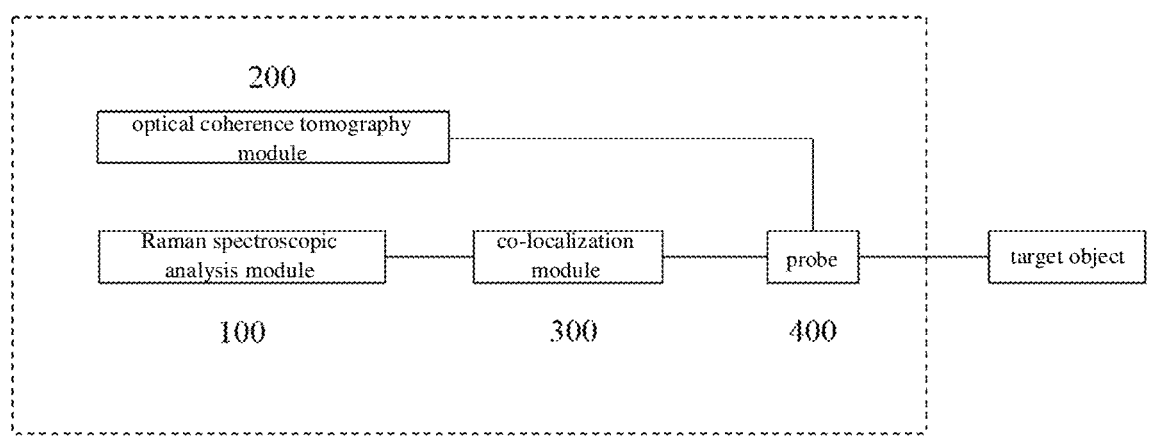
FIG. 1 shows a block diagram of a multi-modal imaging device in an embodiment of the present disclosure, wherein a part in a dashed box can correspond to the multi-modal imaging device in the embodiment of the present disclosure.

100: Raman spectroscopic analysis module
101: first light source
102: first beam splitting mirror
103: first coupling objective lens
104: first optical fiber
105: first lens group
115: collective lens
106: first dichroscope
106': second dichroscope
107: grating
108: receiving lens
109: spectrometer
110: middle reflecting mirror
SW1: first light source switch
200: optical coherence tomography module
201: second light source
202: beam splitter
203: interferometer
204: coupling optical fiber
204': second optical fiber
205: scanning sub-module
205': remote scanning sub-module
206: detector
207: second lens group
217: second focusing lens
227: diffraction lens
208: reflecting mirror
209: circulator
SW2: second light source switch
300: co-localization module
301: first flip mirror
302: second flip mirror
303: first scanning galvanometer
304: second scanning galvanometer
400: probe
401: shell
402: detection window
501: detection optical fiber
502: detection lens
A1: concerned area
A1': sampling area
NBI: narrow-band imaging module
WLR: white light endoscope module
BP: band-pass fiber
NF: notch filter
BP-oct: band-pass fiber arranged on tail end of side, close to target object, of central fiber core group configured to transmit imaging detection light
BP-rs: band-pass fiber arranged on tail end of side, close to target object, of peripheral fiber core group configured to transmit Raman spectroscopy excitation light

DETAILED DESCRIPTION

In order to make objectives, technical solutions and advantages of the present disclosure more obvious, the exemplary embodiments of the present disclosure will be described below with reference to detailed description for the accompanying drawings. Apparently, the described embodiments are only a part of the embodiments of the present disclosure, not all the embodiments. It should be understood that the present disclosure is not limited by the exemplary embodiments described herein.

In the present description and the accompanying drawings, the basically same or similar steps and elements are represented by the same or similar reference numerals in the accompanying drawings, and repeated description for these steps and elements will be omitted. At the same time, in the description of the present disclosure, terms "first", "second" and the like are only for descriptive purposes, but cannot be understood as indicating or implying the relative importance or order.

In the prior art, it is known that a cancer/tumor is diagnosed/screened by using Raman spectroscopy and optical coherence tomography. However, information obtained by using Raman spectroscopy and optical coherence tomography needs to be spatially co-localized, that is to say, the spatially same area should be detected/tested by Raman spectroscopy and optical coherence tomography. Or else, obtaining Raman spectroscopic information and optical coherence tomographic information which are spatially inconsistent is not beneficial to improving the accuracy (such as spatial accuracy) and efficiency of diagnosis/screening.

Besides, the speed of Raman spectroscopy test is lower, and at the same time, it may take too much time to obtain Raman spectroscopic information and optical coherence tomography.

Finally, a probe with a smaller size and a multi-modal endoscope based on Raman spectroscopy and optical coherence tomography are not provided in the prior art.

In order to solve the above-mentioned technical problem, the present disclosure provides a multi-modal imaging device. In addition to a Raman spectroscopic analysis module and an optical coherence tomography module, the multi-modal imaging device further includes a co-localization module which can control sampling positions where a target object is detected by the Raman spectroscopic analysis module and/or the optical coherence tomography module. Therefore, by controlling the sampling positions for detecting the target object, the multi-modal imaging device in the present disclosure can achieve spatial co-localization detection based on Raman spectroscopy and optical coherence tomography.

Besides, the multi-modal imaging device in the present disclosure can also reduce areas required to be tested for Raman spectroscopic analysis, that is to say, it is unnecessary to perform Raman spectroscopic analysis on all areas. For example, it is only necessary to control a first sampling position of Raman spectroscopy by the co-localization module, thereby analyzing the concerned area in the image obtained by the optical coherence tomography module, in this way, the defect of low speed of Raman spectroscopic analysis test is avoided to a great extent, the advantages of high accuracy and high specificity of Raman spectroscopic analysis are still utilized, and then, the overall test efficiency is increased in a cooperative mode. Obviously, in such a mode, two kinds of spatially co-localized information are also obtained.

Finally, in the multi-modal imaging device in the present disclosure, focusing lenses are arranged in the probe, so that the size of the probe can be reduced, which is beneficial to integration into an existing endoscope system.

The above-mentioned operating device provided by the present disclosure will be described in detail below with reference to the accompanying drawings.

FIG. 1 shows a schematic diagram of a multi-modal imaging device according to an embodiment of the present disclosure.

Refer to FIG. 1, the multi-modal imaging device may include a Raman spectroscopic analysis module 100, an optical coherence tomography module 200, a co-localization module 300, and a probe 400. Full lines among all the modules (including the probe) in FIG. 1 schematically show a light path of Raman spectroscopy excitation light from the Raman spectroscopic analysis module 100 and a light path of imaging detection light from the optical coherence tomography module 200, and the Raman spectroscopy excitation light and the imaging detection light detect and test the target object after coupled in the probe. In an implementation according to FIG. 1, the concerned area (such as a possible lesion area in a body of a patient) of the target object is obtained by an imaging device (not shown, such as a white light endoscope module and/or a narrow-band imaging module of an endoscope) different from the multi-modal imaging device.

In an embodiment, for example, in an image of the target object obtained by the white light endoscope module and/or the narrow-band imaging module of the endoscope, a predetermined area can be determined as the concerned area of the target object by manual operation from a doctor.

In another embodiment, in the image of the target object obtained by the white light endoscope module and/or the narrow-band imaging module of the endoscope, the predetermined area can also be determined as the concerned area of the target object by a processing module of the multi-modal imaging device according to a predetermined image processing algorithm.

The co-localization module 300 is configured to control the first sampling position of the excitation light in the Raman spectroscopic analysis module 100 to move to basically overlap with the concerned area; the optical coherence tomography module 200 is configured to perform imaging detection on the first sampling position (i.e., the concerned area), so that the first sampling position and the second sampling position (from the optical coherence tomography module 200) are spatially co-localized in the concerned area. However, the present disclosure is not limited to such a specific implementation. For example, although it is not shown, the co-localization module 300 in the present disclosure may also control the second sampling position of the optical coherence tomography module 200 to move to basically overlap with the concerned area, and the sampling position is analyzed and detected by using the Raman spectroscopic analysis module 100, so that spatial co-localization is achieved in the concerned area. In addition, the implementation of the present disclosure may further include that the first sampling position and the second sampling position are controlled simultaneously and/or synchronously to scan, analyze and detect the concerned area.

In another implementation according to FIG. 1, the optical coherence tomography module 200 is configured to obtain a tissue structure image of the target object by using imaging detection light and determine the concerned area of the target object, and the co-localization module 300 is configured to control the (first) sampling position of the excitation light in the Raman spectroscopic analysis module 100 according to the determined concerned area, thereby obtaining Raman spectroscopic information of different positions in the concerned area. However, the present disclosure is not limited thereto. For example, although it is not shown, the Raman spectroscopic analysis module 100 may also be configured to determine the concerned area of the target object and control the second sampling position of the optical coherence tomography module 200 to scan for imaging in the concerned area, thereby obtaining a tissue structure image and axial information in the concerned area. Obviously, no matter whether the first sampling position of the Raman spectroscopic analysis module 100 or the second sampling position of the optical coherence tomography module 200 is controlled, the Raman spectroscopic information and the tissue structure image which are spatially co-localized can be obtained in the present disclosure by using the co-localization module 300. The skilled in the art can adopt a corresponding implementation based on an actual situation.

A relationship among all the modules in FIG. 1 is only illustrative and exemplary, and is not intended to limit a specific control mode and a specific connection relationship of the co-localization module 300.

It can be seen from FIG. 1 that the co-localization module 300 in the present disclosure makes operating personnel capable of controlling the first sampling position of the Raman spectroscopy excitation light, so that the first sampling position basically overlaps with the concerned area; and then, the second sampling position covers (such as by scanning) the first sampling position, in this way, the Raman spectroscopic information and a tissue structure/morphological image which are spatially co-localized can be obtained. Besides, in a variant implementation, the optical coherence tomography module 200 can rapidly obtain tissue structure image and determine the concerned area of the target object, and then further guide the sampling position of the Raman spectroscopy excitation light, thereby obtaining diagnosis information with high accuracy and specificity on a high-risk position of the target object.

Figure 2:
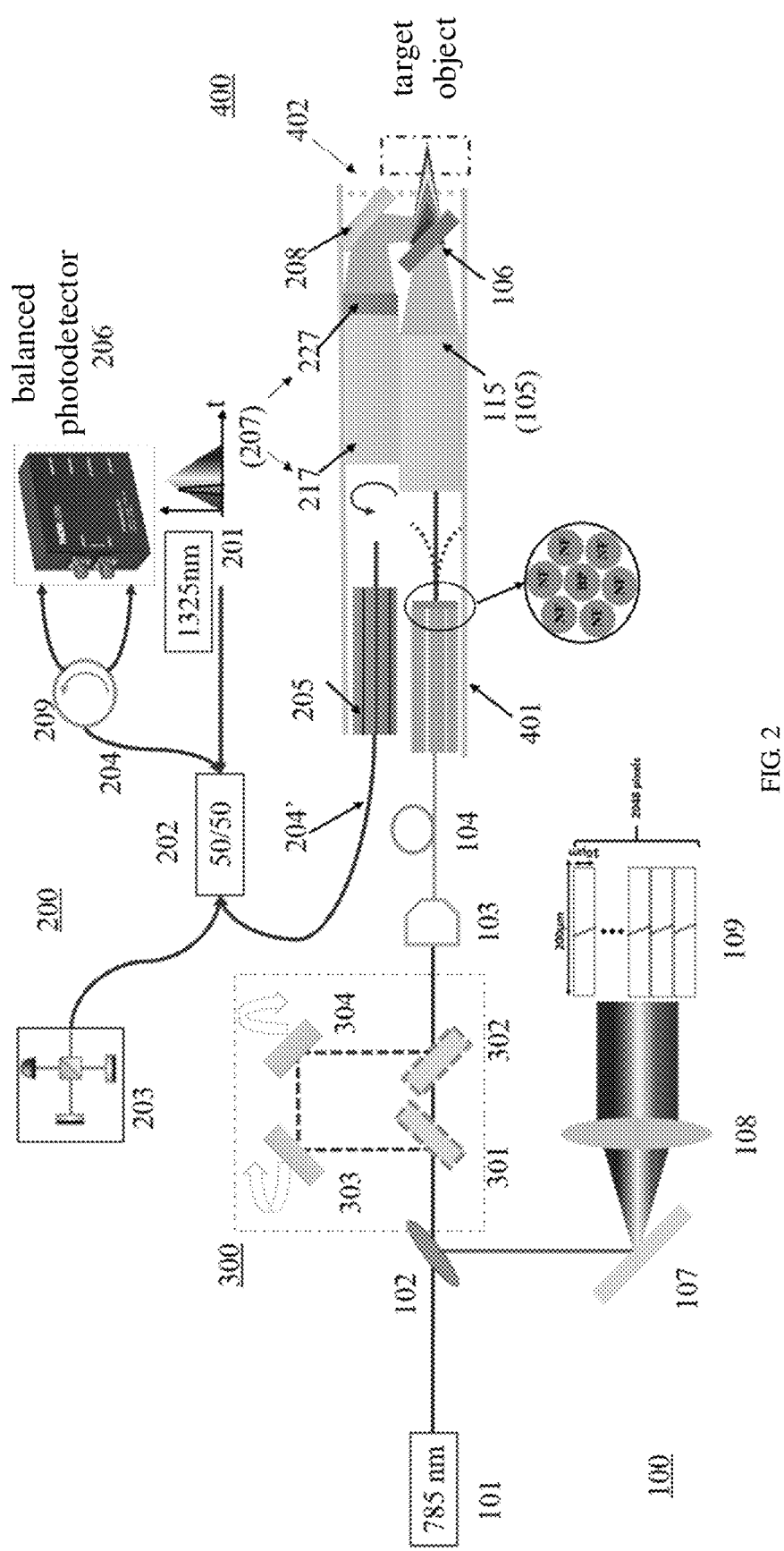
FIG. 2 shows a schematic diagram of a multi-modal imaging device according to an implementation of an embodiment of the present disclosure.

FIG. 2 shows a schematic diagram of a multi-modal imaging device according to an implementation of an embodiment of the present disclosure.

Specifically, refer to FIG. 2, a first light source 101 of the Raman spectroscopic analysis module 100 adopts a Raman excitation light source of which a wavelength is 785 nm. Any known light source applicable to the Raman spectroscopy excitation light in the art can be selected as the first light source 101, and the Raman excitation light source of which the wavelength is 785 nm in this implementation is only an example. A first beam splitting mirror 102, the co-localization module 300, a first coupling objective lens 103, a first optical fiber 104, a first lens group 105 and a first dichroscope 106 are arranged along an emergent light path of the Raman spectroscopy excitation light. The first lens group 105 consists of a collective lens 115. The Raman spectroscopic analysis module 100 is further provided with a grating 107 configured to split reflected light from the first beam splitting mirror 102, a receiving lens 108 is configured to receive emergent light from the grating 107, and a spectrometer 109 is configured to receive emergent light from the receiving lens 108.

By adjusting parameters of the collective lens 115, a size of a light spot of Raman spectroscopy on the target object can be controlled. As required, the size of the light spot can be adjusted within a range from 5 μm to 1 mm (diameter). In a preferred implementation, by using the collective lens 115, the size of the light spot of the Raman spectroscopy excitation light from the first light source 101 is basically the same as the size of the concerned area. In addition, in an alternative implementation, the first lens group may also adopt a focusing lens including a focusing lens with high dispersion and/or a high numerical aperture. For example, a usable focusing lens has an effective focal length of 2-3 mm, a working distance of 1 mm, and a numerical aperture expressed as N/A=0.5. The lens with high dispersion can increase an axial field of view, and the high numerical aperture is beneficial to the improvement of a resolution and an imaging signal-to-noise ratio. In this implementation of the present disclosure, by using the collective lens 115, the size of the light spot of the Raman spectroscopy excitation light from the first light source 101 is consistent with the size of the concerned area, which is preferable due to the conservation of time for obtaining the Raman spectroscopic information.

Splitting light by using the lens with high dispersion and the grating at the same time is beneficial to obtaining Raman spectroscopic information of different depths of the target object at the same time and improving the test speed.

FIG. 2 schematically describes the enlarging of a cross section of a side, close to the target object, of the first optical fiber 104. A central fiber core group consisting of at least one fiber core on a central part of a multi-core optical fiber in the probe 400 is configured to transmit Raman spectroscopy excitation light from the first light source 101, and a plurality of peripheral fiber core groups of groups consisting of at least one fiber core surrounding the central part in the multi-core optical fiber are configured to transmit the Raman spectroscopy scattering signal light; a band-pass (BP) fiber represented by BP is arranged on a tail end of a side, close to the target object, of the central fiber core group, and notch fibers (NF) represented by NF are arranged on tail ends of sides, close to the target object, of the peripheral fiber core groups. That is to say, the Raman spectroscopy excitation light excites Raman spectroscopy of the target object through the band-pass (BP) filter, a Raman scattering light signal filters background noise through the notch filters (NF) and long-pass filters (not shown), and such settings are beneficial to increasing the signal-to-noise ratio of the signal.

For acquisition of the Raman spectroscopic information, the present disclosure is not limited to above specific optical fiber layout. Some other layout modes are given in FIG. 3 in the accompanying drawings of the description of the present disclosure.

Figure 3:
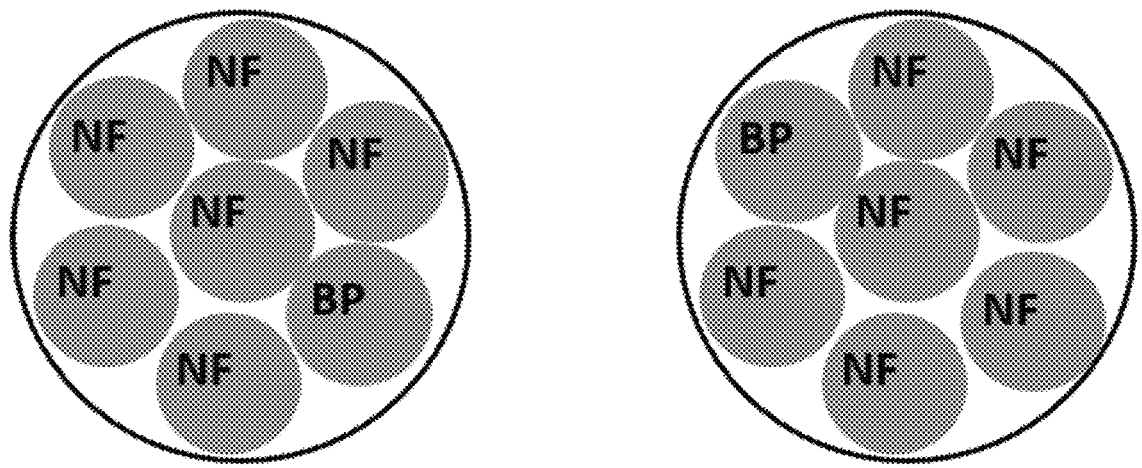
FIG. 3 shows a layout mode of an alternative optical fiber in a multi-core optical fiber used in a multi-modal imaging device according to an implementation of an embodiment of the present disclosure.

However, a preferred optical fiber layout mode in the present disclosure is a layout mode shown in FIG. 2 in the accompanying drawings of the description. Such preferred central symmetry layout in the present disclosure is beneficial to obtaining a better Raman spectroscopic signal than other layout modes (such as layout with lower symmetry). For example, it has been found that, compared with the following layout modes, the layout mode shown in FIG. 2 in the accompanying drawings of the description of the present disclosure allows to obtain a higher signal-to-noise ratio: an optical fiber configured to transmit a Raman spectroscopy scattering signal is arranged asymmetrically relative to an optical fiber configured to transmit the Raman spectroscopy excitation light, for example, a gap where the optical fiber configured to transmit the Raman spectroscopy scattering signal is not arranged exists around a position adjacent to the optical fiber configured to transmit the Raman spectroscopy excitation light (in the case that a part of an outer surface of the optical fiber configured to transmit the Raman spectroscopy excitation light is in contact with a wall of the optical fiber), for example, a layout mode shown in FIG. 3 is included).

The optical coherence tomography module 200 includes a second light source 201, a beam splitter 202, an interferometer 203, a coupling optical fiber 204, a second optical fiber 204', a scanning sub-module 205, a detector 206, a second lens group 207, a reflecting mirror 208, and a circulator 209. Any known light source applicable to optical coherence tomography in the art can be selected as the second light source. As an example, the second light source 201 adopts a swept light source of which a wavelength is 1325 nm, and the detector 206 is a balanced photodetector. The second lens group 207 consists of a second focusing lens 217 and a diffraction lens 227. The scanning sub-module 205 is a piezoelectric ceramic tube.

By using the second focusing lens 217, a size of a light spot of incident light emitted by the second light source 201 on the target object can be controlled. As required, the size of the light spot can be adjusted within a range from 5 μm to 1 mm (diameter). In addition, a usable focusing lens includes a focusing lens with high dispersion and/or a high numerical aperture. For example, the usable focusing lens has an effective focal length of 2-3 mm, a working distance of 1 mm, and a numerical aperture expressed as N/A=0.5. The lens with high dispersion can increase an axial field of view, and the high numerical aperture is beneficial to the improvement of a resolution and an imaging signal-to-noise ratio. In addition, in this implementation of the present disclosure, it is found that the diffraction lens 227 can compensate the dispersion, improve a wavelength and a bandwidth, and improve the resolution, thereby improving the imaging quality.

The piezoelectric ceramic tube is a known scanning device in the art. In the scanning sub-module 205 in the present disclosure, the optical fiber is coaxially fixed to the piezoelectric ceramic tube, and the piezoelectric ceramic tube piezoelectrically deforms after pressed, thereby leading to the bending of an end of a single-mode optical fiber; when external voltages applied to two pairs (four axes) of electrodes of an x axis and a y axis of the piezoelectric ceramic tube are modulation voltages, two-dimensional scanning is achieved; when vibration frequencies of the axes of the piezoelectric ceramic tube and a self-frequency of the single single-mode optical fiber are resonant, the maximum scanning amplitude is achieved; and therefore, a size of a scanned area and a scanning speed are respectively controlled by controlling amplitudes and frequencies of the voltages applied to the piezoelectric ceramic tube. When the modulation voltages applied to the x axis and the y axis are orthogonal sine signals, a spiral scanning trace is generated. By scanning by using the piezoelectric ceramic tube, rapid three-dimensional tissue structure 3D-OCT image can be achieved.

Preferably, the detector 206 of the device in the present disclosure includes an acquisition system based on a high-speed digital-to-analog converter and an FPGA, which can achieve reconstruction and display of a tissue structure image of a video flow. An FPGA system converts a detection light interference signal into a sample structure grayscale map and an attenuation coefficient grayscale map which are transmitted to an upper computer so as to be displayed.

The co-localization module 300 includes a first flip mirror 301 and a second flip mirror 302 which are arranged between the first beam splitting mirror 102 and the first coupling objective lens 103 as well as a first scanning galvanometer 303 and a second scanning galvanometer 304 which are matched with the two flip mirrors.

The probe 400 includes a shell 401 and a detection window 402.

One part of the first optical fiber 104, the first lens group 105 and the first dichroscope 106 are arranged in the probe 400; and one part of the second optical fiber 204', the scanning sub-module 205, the second lens group 207 and the reflecting mirror 208 are arranged in the probe 400.

By such a design of the probe in the present disclosure, an internal diameter of the probe can be reduced to 2-10 mm (which is much smaller than the size of 5 cm used in a traditional light path design in the prior art), which is beneficial to integration into a working channel of an existing endoscope system to reduce damage possibly brought by endoscope detection, thereby being beneficial to clinical application.

A working mode of the multi-modal imaging device according to an implementation of an embodiment of the present disclosure will be described below.

The excitation light from the first light source 101 sequentially passes through the first beam splitting mirror 102 and the co-localization module 300 and enters the first optical fiber 104 after collimated by the first coupling objective lens 103. The emergent light from the first optical fiber 104 passes through the collective lens 115, wherein the first optical fiber 104 is a multi-core optical fiber. Parameters of the collective lens 115 may be selected to control a size of a light spot from Raman spectroscopy detection light. In an implementation of the present disclosure, a diameter of the light spot can be adjusted within a range from 5 μm to 1 mm. The target object is detected through the detection window 402 after emergent light from the collective lens 115 is optically coupled with the imaging detection light from the optical coherence tomography module 200 through the first dichroscope 106. Raman spectroscopy scattering light from the target object is returned along a light path approximately the same as a light path of the excitation light and is reflected by the first beam splitting mirror 102 to enter the grating 107 so as to be split, and the emergent light from the grating 107 is tested through the spectrometer 109 after passing through the receiving lens 108.

After passing through the beam splitter 202, the imaging detection light from the second light source 201 enters the probe 400 through the second optical fiber 204'. Emergent light from the second optical fiber 204' in the probe enters the second focusing lens 217, and then enters the reflecting mirror 208 through the diffraction lens 227. Parameters of the second focusing lens 217 may be selected to control a size of a light spot of the imaging detection light. In an implementation of the present disclosure, a diameter of the light spot can be adjusted within a range from 5 μm to 1 mm. It is found that, by using the diffraction lens 227 in the second lens group 207, the imaging resolution is improved. The emergent light from the reflecting mirror 208 enters the first dichroscope 106 so as to be coupled with the Raman spectroscopy excitation light passing through the first dichroscope 106, and then, the target object is imaged through the detection window 402. In this implementation, the second optical fiber 204' is coaxially fixed to the piezoelectric ceramic tube, and the piezoelectric ceramic tube includes two pairs of axes (four axes in total) which are arranged around the second optical fiber 204' in a square mode. The piezoelectric ceramic tube piezoelectrically deforms after pressed, thereby leading to the bending of the end of the optical fiber; and when the external voltages applied to the two pairs (four axes) of electrodes of the x axis and the y axis of the piezoelectric ceramic tube are the modulation voltages, two-dimensional scanning is achieved. The scattering light from the target object is returned along a light path basically the same as the incident light and is detected by the detector 206 after passing by the beam splitter 202, the interferometer 203, and the circulator 209.

In this implementation, by adjusting an angle of a light path between the first flip mirror 301 and the second flip mirror 302 relative to a light path between the first beam splitting mirror 102 and the first coupling objective lens 103, the co-localization module 300 is switchable between the first mode and the second mode.

In the first mode, when the mirror surfaces of the first flip mirror 301 and the second flip mirror 302 are parallel to the light path between the first beam splitting mirror 102 and the first coupling objective lens 103, the existence of the co-localization module 300 does not affect an incident direction of the light path between the first beam splitting mirror 102 and the first coupling objective lens 103, and thus, the first sampling position of the Raman spectroscopy excitation light on the target object is not affected.

In the second mode, when the mirror surfaces of the first flip mirror 301 and the second flip mirror 302 are not parallel to the light path between the first beam splitting mirror 102 and the first coupling objective lens 103, for example, they are arranged at angles shown in FIG. 2, the first flip mirror 301 is configured to receive and reflect light transmitted by the first beam splitting mirror 102, the first scanning galvanometer 303 is configured to receive and reflect reflected light from the first flip mirror 301, the second scanning galvanometer 304 is configured to receive and reflect reflected light from the first scanning galvanometer 303, the second flip mirror 302 is configured to receive and reflect reflected light from the second scanning galvanometer 304, and the first coupling objective lens 103 is configured to receive reflected light from the second flip mirror. The co-localization module 300 in the second mode will affect the Raman spectroscopy excitation light. For example, by rotating the first scanning galvanometer 303 and/or the second scanning galvanometer 304 around a preset axis, the emergent light from the first beam splitting mirror 102 will be deviated from a direction of an original light path (such as a direction of the light path in the first mode) at a certain angle, which leads to a change of a position of the incident light from the first coupling objective lens 103. As a result, the sampling position of the Raman spectroscopy excitation light on the target object is changed. In the present implementation, the first scanning galvanometer 303 and the second scanning galvanometer 304 can respectively rotate along axes orthogonal to each other.

However, the present disclosure is not limited thereto, and spatial orientations of the axes for rotating the first scanning galvanometer 303 and the second scanning galvanometer 304 can be set by the skilled in the art on the basis of above disclosure according to an actual situation or as required. An axis with a certain orientation in a given coordinate system can be selected, and thus, a position/angle/shape of the Raman spectroscopy excitation light is affected in different modes by rotating the first scanning galvanometer 303 and the second scanning galvanometer 304. In this implementation, each of the first scanning galvanometer 303 and the second scanning galvanometer 304 adopts the MEMS-driven reflecting mirror. However, the present disclosure is not limited thereto, and other optical elements, such as the Galvo galvanometer, with the same function can be used by the skilled in the art on the basis of above disclosure according to an actual situation or as required.

The multi-modal imaging device according to this implementation of the embodiment of the present disclosure has a plurality of operating modes, some of which are only exemplarily listed hereinafter.

Figure 4A:
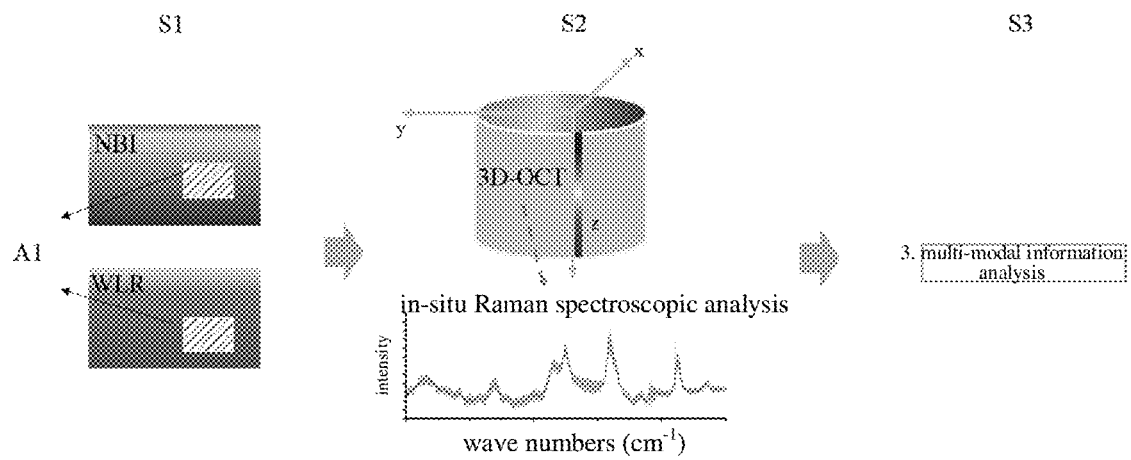
FIG. 4*a* shows a co-localization detection process actually generated during operation of a multi-modal imaging device according to an implementation of an embodiment of the present disclosure.

As a first operating mode, a co-localization detection process thereof may refer to FIG. 4*a*. In this operating mode, by using the second focusing lens 217, a size of a light spot of the optical coherence tomography module 200 on the target object is smaller than a size of the first sampling position. In step S1, the target object is imaged by NBI or WLR, and the concerned area A1 (a shadow part with slashes) is recognized. The recognition process can be performed by operating personnel or a doctor or by means of an algorithm. In a preferred implementation, the concerned area (a tumor or suspected tumor part) is automatically recognized by a deep learning model (CNN) image segmentation algorithm. In step S2, the first sampling position of the Raman spectroscopic analysis module 100 is moved by the co-localization module 300 so as to basically overlap with the concerned area A1, and Raman spectroscopic analysis is performed on the area; the Raman spectroscopic information can reflect structural information, such as lipid and proteins, of specific molecules, and a signal intensity is related to a concentration; and therefore, the selection of the specific molecules related to the occurrence of cancer lesion is very beneficial to cancer screening and test. Next, the optical coherence tomography module 200 performs scanning imaging in the first sampling position by using the scanning sub-module 205 thereof to obtain the tissue structure image spatially co-localized with the first sampling position. In step S3, the obtained multi-modal information which is spatially co-localized is analyzed. Preferably, analysis is performed by fusion by using the LSTM algorithm. Thus, it can be seen that the multi-modal imaging device in the present disclosure controls the first sampling position of the Raman spectroscopic analysis module 100 by using the co-localization module 300 to basically overlap with the concerned area, and performs scanning imaging in this area by using the optical coherence tomography module 200, which allows to obtain the Raman spectroscopic information and tissue structure image information which are spatially co-localized. Due to high spatial consistency, the multi-modal information of the same precise position in the true sense is obtained in the present disclosure, which is beneficial to improvement of the correlation between the Raman spectroscopic information and the tissue structure image information, thereby improving the accuracy and efficiency of diagnosis/screening. It is expected to point out that the present disclosure is not limited to such one specific implementation, for example, although it is not shown, the co-localization module 300 in the present disclosure can also control the second sampling position of the optical coherence tomography module 200 to move to basically overlap with the concerned area A1, and the sampling position is analyzed and detected by using the Raman spectroscopic analysis module 100, so that spatial co-localization is achieved in the concerned area.

Figure 4B:
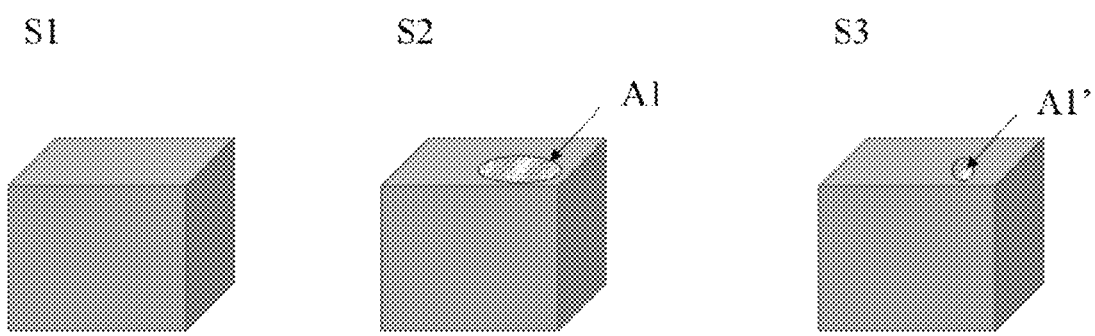
FIG. 4b shows another co-localization detection process actually generated during operation of a multi-modal imaging device according to an implementation of an embodiment of the present disclosure.

As another operating mode, a co-localization detection process thereof may refer to FIG. 4*b*. In this mode, the first lens group 105 in the Raman spectroscopic analysis module 100 adopts a focusing lens, and the size of the first sampling position is smaller than the size of the light spot of the optical coherence tomography module 200 on the target object. In this mode, the optical coherence tomography module 200 is configured to obtain the tissue structure image of the target object by using the imaging detection light and determine the concerned area of the target object, and the co-localization module 300 is configured to control the first sampling position of the excitation light in the Raman spectroscopic analysis module 100 according to the determined concerned area of the target object, thereby obtaining the Raman spectroscopic information of different positions in the concerned area. In step S1, a 3D-OCT image is obtained after spiral scanning performed by the piezoelectric ceramic tube of the scanning sub-module 205. In step S2, the concerned area A1 (a shadow part with slashes) is recognized. The recognition process can be performed by operating personnel or a doctor or by means of an algorithm. In a preferred implementation, the concerned area (a tumor or suspected tumor part) is automatically recognized by a deep learning model (CNN) image segmentation algorithm, and a Raman spectroscopy sampling position is arranged and navigated by the co-localization module. In step S3, the sampling position A1' (a shadow part with slashes) of the Raman spectroscopic analysis module is controlled by the co-localization module 300, thereby obtaining the Raman spectroscopic information in the concerned area A1. The Raman spectroscopic information can reflect structural information, such as lipid and proteins, of specific molecules, and a signal intensity is related to a concentration. Therefore, the selection of the specific molecules related to the occurrence of cancer lesion is very beneficial to cancer screening and test. Optionally, the multi-modal information (OCT tissue structure image and co-localized Raman spectroscopy data) is fused by using the LSTM algorithm, which can further improve the accuracy of cancer diagnosis. Thus, it can be seen that the co-localization module 300 in the present disclosure achieves high-efficiency cooperative operation of Raman spectroscopic analysis and optical coherence tomography by controlling the sampling position of the Raman spectroscopy excitation light in the specific concerned area, so that high-accuracy and high-specificity screening and diagnosis for cancers/tumors can be achieved. As mentioned above, the present disclosure is not limited thereto, it is also possible that the concerned area A1 is obtained by using the Raman spectroscopic analysis module 100 by means of an appropriate lens and operating mode, and the second sampling position of the optical coherence tomography module 200 is controlled to scan in the concerned area A1 so as to obtain the Raman spectroscopic information and the tissue structure image information which are spatially co-localized. Such a mode has the advantages that the concerned area can be obtained based on two-dimensional Raman spectroscopic information, and the corresponding axial tissue structure image information is further obtained by using 3D-OCT imaging. The skilled in the art can select a specific corresponding implementation on the basis of the above-mentioned disclosed contents according to different concerns.

The multi-modal imaging device according to the above-mentioned implementation of the embodiment of the present disclosure can be used in scenarios of hard lens test for glioma, digestive tract tumors, surgical tumors on the head and the neck, thyroid tumors and the like to realize the test of transverse planar incisal edges of tissues.

Figure 5:
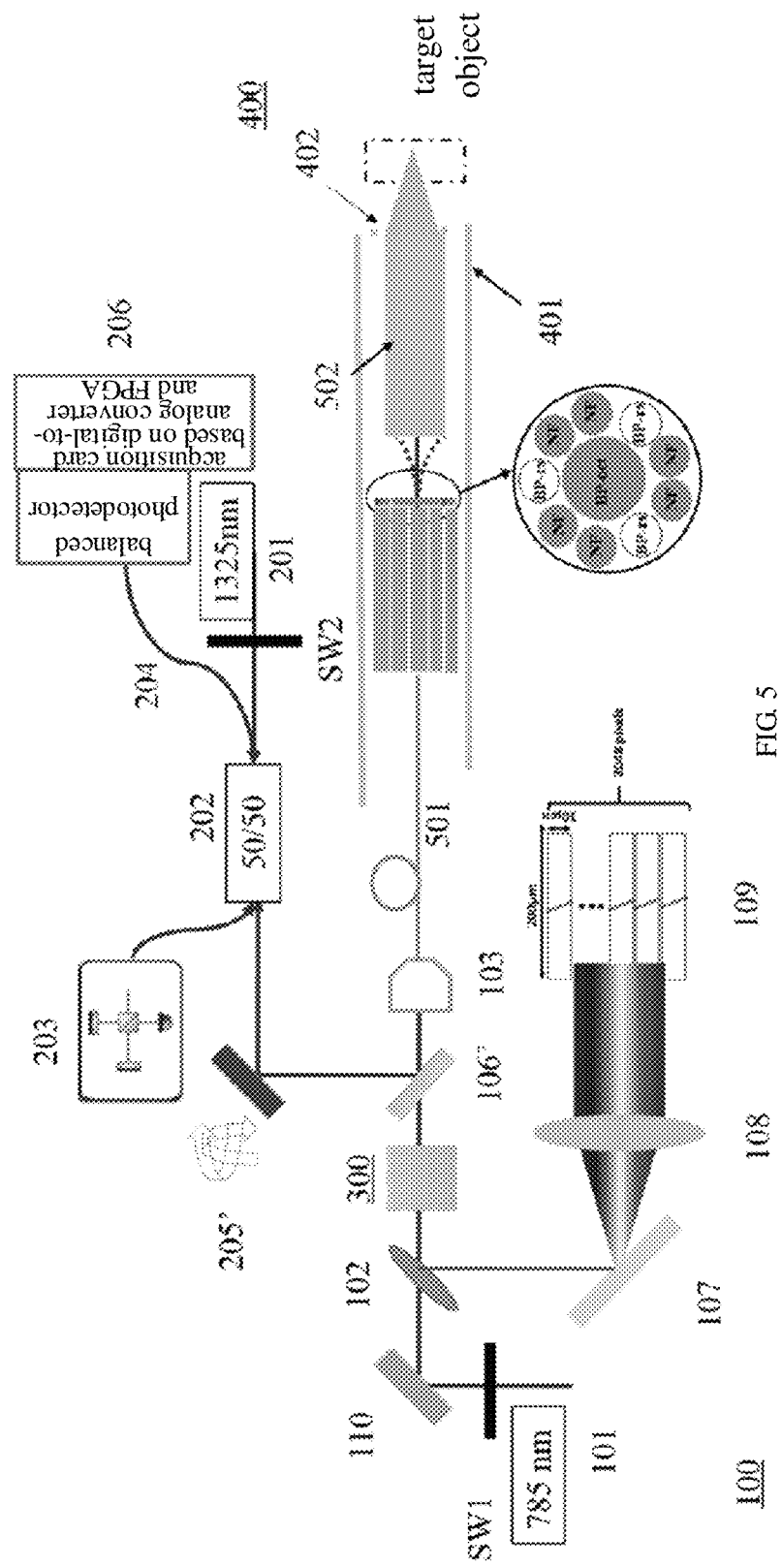
FIG. 5 shows a schematic diagram of a multi-modal imaging device according to another implementation of an embodiment of the present disclosure.

FIG. 5 shows a schematic diagram of a multi-modal imaging device according to another implementation of an embodiment of the present disclosure.

The most important difference between the multi-modal imaging device according to another implementation involved in FIG. 5 in the accompanying drawings of the description of the present disclosure and the multi-modal imaging device according to the implementation involved in FIG. 2 in the accompanying drawings of the description of the present disclosure lies in that the excitation light from the Raman spectroscopic analysis module and the imaging detection light from the optical coherence tomography module are coupled by using the dichroscope before entering the probe, and the single lens group and the same optical fiber bundle are shared in the probe without distinguishing the first lens group for the Raman spectroscopic analysis module and the second lens group for the optical coherence tomography module. The multi-modal imaging device according to another implementation involved in FIG. 5 in the embodiment of the present disclosure has the advantages that the size of the probe can be further reduced and even reduced to 2-5 mm, which is more beneficial to integration into a working channel of an existing endoscope system to reduce damage possibly brought by endoscope detection, thereby being more beneficial to clinical application.

Specifically, refer to FIG. 5, a first light source 101 of the Raman spectroscopic analysis module 100 adopts a Raman excitation light source of which a wavelength is 785 nm. A first light source switch SW1, a middle reflecting mirror 110, a first beam splitting mirror 102, the co-localization module 300, a second dichroscope 106', a first coupling objective lens 103, a detection optical fiber 501 and a detection lens 502 are arranged along an emergent light path of the Raman spectroscopy excitation light. The shown detection lens 502 is a detection focusing lens. The Raman spectroscopic analysis module 100 is further provided with a grating 107 configured to split reflected light from the first beam splitting mirror 102, a receiving lens 108 is configured to receive emergent light from the grating 107, and a spectrometer 109 is configured to receive emergent light from the receiving lens 108. The detection optical fiber 501 is a multi-core optical fiber.

The detection focusing lens has the same or similar effects as the collective lens 115 and the second focusing lens 217 in the implementation involved in FIG. 2 in the accompanying drawings of the description of the present disclosure. The detection focusing lens can also be selected based on performances and parameters such as a size of a light spot, high dispersion and/or a high numerical aperture. The excitation light from the Raman spectroscopic analysis module 100 and the imaging detection light from the optical coherence tomography module 200 are coupled by the second dichroscope 106' before entering the detection optical fiber, so that the coupled light can be focused and controlled by using a single optical fiber and a single detection focusing lens. By such a setting, the size of the probe can be further reduced, for example, the size of the probe can be reduced to 2-5 mm, thereby being more applicable to an existing endoscope system. Due to a smaller internal diameter, the probe can be used in scenarios of soft lens test for gastric tumors, digestive tract tumors, and bladder tumors. Preferably, in order to relatively accurately obtain the spectroscopic information and the image information which are spatially co-localized, the detection focusing lens is adopted, so that sizes of light spots of the excitation light from the Raman spectroscopic analysis module 100 and the imaging detection light from the optical coherence tomography module 200 are smaller than the size of the concerned area. In this way, the first sampling position and the second sampling position can be controlled to scan in the concerned area, and information obtained after scanning is valuable spatially co-localized auxiliary information for diagnosis/screening.

FIG. 5 schematically describes the enlarging of a cross section of a side, close to the target object, of the detection optical fiber 501. A central fiber core group consisting of at least one fiber core on a central part of a multi-core optical fiber is configured to transmit the imaging detection light from the second light source 201 and light from the target object and configured to obtain the tissue structure image of the target object, and a plurality of peripheral fiber core groups of groups consisting of at least one fiber core surrounding the central part in the multi-core optical fiber are respectively configured to transmit Raman spectroscopy excitation light and Raman spectroscopy scattering signal light from the first light source 101. In this implementation, the peripheral fiber core groups configured to transmit the Raman spectroscopy excitation light and the peripheral fiber core groups configured to transmit the Raman spectroscopy scattering signal light are arranged alternatively, and one peripheral fiber core group configured to transmit the Raman spectroscopy excitation light is arranged every three peripheral fiber core groups configured to transmit the Raman spectroscopy scattering signal light. A band-pass fiber represented by BP-oct is arranged on a tail end of a side, close to the target object, of the central fiber core group, band-pass (BP) fibers represented by BP-rs are arranged on tail ends of sides, close to the target object, of the peripheral fiber core groups configured to transmit the Raman spectroscopy excitation light, and notch fibers (NF) represented by NF are arranged on tail ends of sides, close to the target object, of the peripheral fiber core groups configured to transmit the Raman spectroscopy scattering signal light. That is to say, the Raman spectroscopy excitation light excites Raman spectroscopy of the target object through the band-pass (BP) filter, a Raman scattering light signal filters background noise through the notch filters (NF) and long-pass filters (not shown), and such settings are beneficial to increasing the signal-to-noise ratio of the signal.

For a layout mode of the central fiber core group configured to transmit the OCT imaging detection light in the multi-modal imaging device according to another implementation involved in FIG. 5 in the accompanying drawings of the description of the present disclosure, the present disclosure is not limited thereto. A layout mode of the fiber core group used for the OCT imaging detection light in the multi-modal imaging device according to another implementation involved in FIG. 5 in the accompanying drawings of the description of the present disclosure may also be like that shown in FIG. 6 in the accompanying drawings of the description, that is, the a non-central fiber core group is used for the OCT imaging detection light. However, it has been found that the central fiber core group used for transmitting the OCT imaging detection light and returned scattering light (a layout mode shown in FIG. 5) has a higher resolution than fiber cores on other positions (such as a layout mode shown in FIG. 6). It has been found that, if the fiber core group for transmitting the OCT imaging detection light and the returned scattering light and other fiber core groups adopt the central fiber core group for transmission, a Rayleigh range of a focused light spot will be reduced, so that the central fiber core group has a higher resolution during imaging as comparison with an "eccentric" fiber core group.

Figure 6:
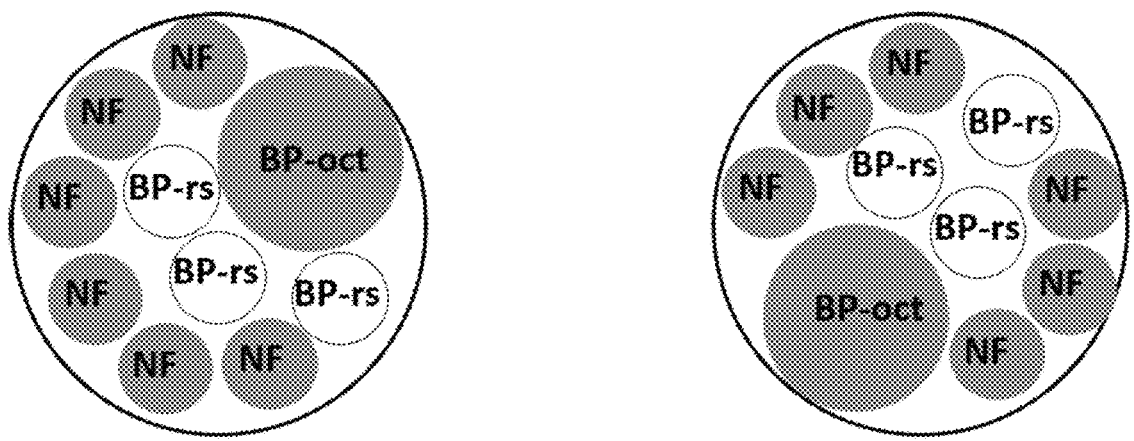
FIG. 6 shows a layout mode of an alternative optical fiber in a multi-core optical fiber used in a multi-modal imaging device according to another implementation of an embodiment of the present disclosure.

For the layout of the peripheral fiber core groups configured to transmit the Raman spectroscopy excitation light and scattering signal light in the multi-modal imaging device according to another implementation involved in FIG. 5 in the accompanying drawings of the description of the present disclosure, the present disclosure is not limited to the layout shown in FIG. 5, and a layout mode of the fiber core groups configured to transmit the Raman spectroscopy excitation light and the Raman spectroscopy scattering signal light in the multi-modal imaging device according to another implementation involved in FIG. 5 in the accompanying drawings of the description of the present disclosure may also be like that shown in FIG. 6 in the accompanying drawings of the description. However, the layout mode in FIG. 5 in the accompanying drawings of the description of the present disclosure is preferred; and fiber cores configured to transmit the Raman spectroscopy excitation light and the Raman spectroscopy scattering signal light are alternatively arranged in the peripheral fiber core groups, so that relative symmetry is still kept, that is, fiber cores configured to transmit the Raman spectroscopy scattering signal light exist around each fiber core configured to transmit the Raman spectroscopy excitation light. Therefore, similar to the layout of optical fiber cores described in the implementation involved in FIG. 2 in the accompanying drawings of the description of the present disclosure, such a layout mode in FIG. 5 in the present disclosure can achieve a higher signal-to-noise ratio than a layout mode (such as FIG. 6) which is asymmetric or lower in symmetry.

As an alternative implementation, in addition to the multi-core optical fiber, fiber cores of a single-mode optical fiber can also be utilized to transmit an OCT light source and signal, and a cladding can be utilized to transmit a Raman light source and signal (not shown).

However, a preferred implementation is an implementation involved in FIG. 5 in the accompanying drawings of the description of the present disclosure, and the layout mode in FIG. 5 can achieve a higher signal-to-noise ratio and resolution.

The optical coherence tomography module 200 includes a second light source 201, a second light source switch SW2, a beam splitter 202, an interferometer 203, a coupling optical fiber 204, a remote scanning sub-module 205', and a detector 206. The second light source 201 adopts a swept light source of which a wavelength is 1325 nm, and the detector 206 is a balanced photodetector and is equipped with an acquisition card based on a digital-to-analog converter and an FPGA. The remote scanning sub-module 205' is an MEMS-driven reflecting mirror. However, the present disclosure is not limited thereto, and the remote scanning sub-module 205' may also adopt a plurality of Galvo galvanometers or other elements capable of achieving a scanning function.

A scanning mode of a remote scanning galvanometer used by the remote scanning sub-module 205' is different from that of the multi-modal imaging device according to the implementation involved in FIG. 2 in the accompanying drawings of the description of the present disclosure. Scanning performed in the multi-modal imaging device according to another implementation involved in FIG. 5 in the accompanying drawings of the description of the present disclosure is performed "line by line", rather than spirally.

The first light source 101 and the second light source 201 which are used in the multi-modal imaging device according to another implementation involved in FIG. 5 in the accompanying drawings of the description of the present disclosure are the same as the first light source 101 and the second light source 201 which are used in the multi-modal imaging device according to the implementation involved in FIG. 2 in the accompanying drawings of the description of the present disclosure.

The co-localization module 300 in the multi-modal imaging device according to another implementation involved in FIG. 5 in the accompanying drawings of the description of the present disclosure is the same as that in the multi-modal imaging device according to the implementation involved in FIG. 2 in the accompanying drawings of the description of the present disclosure. The co-localization module 300 includes a first flip mirror 301 and a second flip mirror 302 which are arranged between the first beam splitting mirror 102 and the first coupling objective lens 103 as well as a first scanning galvanometer 303 and a second scanning galvanometer 304 which are matched with the two flip mirrors.

The probe 400 includes a shell 401 and a detection window 402.

One part of the detection optical fiber 501 and the detection lens 502 are arranged in the probe 400. The detection focusing lens has the same or similar effect as the first and second focusing lenses in the implementation involved in FIG. 2 in the accompanying drawings of the description of the present disclosure. However, the excitation light from the Raman spectroscopic analysis module 100 and the imaging detection light from the optical coherence tomography module 200 are coupled by the second dichroscope 106' before entering the detection optical fiber, so that the coupled light can be focused and controlled by using a single optical fiber (the detection optical fiber 501) and a single detection focusing lens 502. By such a setting, the size of the probe can be further reduced, thereby being more applicable to an existing endoscope system. Due to a smaller internal diameter, the probe can be used in scenarios of soft lens test for gastric tumors, digestive tract tumors, and bladder tumors.

A working mode of the multi-modal imaging device according to another implementation involved in FIG. 5 in the accompanying drawings of the description of the present disclosure.

In the case that the first light source switch SW1 is turned on, the excitation light from the first light source 101 sequentially passes through the middle reflecting mirror 110, the first beam splitting mirror 102, the co-localization module 300 and the second dichroscope 106' and enters the detection optical fiber 501 after collimated by the first coupling objective lens 103. The emergent light from the detection optical fiber 501 passes through the detection lens 502 so as to be focused, wherein the detection optical fiber 501 is a multi-core optical fiber. Parameters of the detection lens 502 may be selected to control a size of a light spot from Raman spectroscopy detection light. In an implementation of the present disclosure, a diameter of the light spot can be adjusted within a range from 5 μm to 1 mm. The target object is detected by the emergent light from the detection lens 502 through the detection window 402. Raman spectroscopy scattering light from the target object is returned along a light path approximately the same as a light path of the excitation light and is reflected by the first beam splitting mirror 102 to enter the grating 107 so as to be split, and the emergent light from the grating 107 is tested through the spectrometer 109 after passing through the receiving lens 108.

In the case that the second light source switch SW2 is turned on, after passing through the beam splitter 202, the imaging detection light from the second light source 201 is reflected by the remote scanning sub-module 205' and is emitted by the remote scanning sub-module 205' to enter the second dichroscope 106'. In this way, the Raman spectroscopy excitation light from the first light source 101 and the imaging detection light from the second light source 201 are optically coupled at the second dichroscope 106'. A scanning mode of the MEMS-driven reflecting mirror used by the remote scanning sub-module 205' is different from that of the multi-modal imaging device according to the implementation involved in FIG. 2 in the accompanying drawings of the description of the present disclosure. Scanning performed in the MEMS-driven reflecting mirror (or a Galvo galvanometer) is to change an angle and/or a position of the imaging detection light entering the first coupling objective lens 103 by rotating around at least one axis. A mode for forming an image in such a scanning mode can refer to FIG. 7b, wherein the image is obtained by "piece by piece" (i.e., line by line).

In this implementation of the present disclosure, test in the two modes can be switched in a time domain by externally triggering the light source switches in the two modes, thereby reducing mutual effects between the modes, and then improving the signal-to-noise ratio. It is very beneficial to ensuring that an acceptable signal-to-noise ratio is kept during test in the two modes respectively in the case that the size of the probe is reduced. Therefore, preferably, the test in the two modes is alternatively performed by externally triggering the light source switches in the two modes so as to obtain an improved signal-to-noise ratio.

Light coupled by the first coupling objective lens 103 enters the detection optical fiber 501 after collimated by the first coupling objective lens 103. The emergent light from the detection optical fiber 501 enters the detection lens 502, and the target object is imaged/detected through the detection window 402. The scattering light from an object sample is returned along a light path basically the same as a light path of the incident light and is detected by the detector 206 after passing by the beam splitter 202 and the interferometer 203.

In this implementation, by adjusting an angle of a light path between the first flip mirror 301 and the second flip mirror 302 relative to a light path between the first beam splitting mirror 102 and the second dichroscope 106', the co-localization module 300 is switchable between the first mode and the second mode. A specific internal structure of the co-localization module 300 is the same as that in FIG. 2 so as not to be shown in FIG. 5.

In the first mode, when the mirror surfaces of the first flip mirror 301 and the second flip mirror 302 are parallel to the light path between the first beam splitting mirror 102 and the second dichroscope 106', the existence of the co-localization module 300 does not affect an incident direction of the light path between the first beam splitting mirror 102 and the second dichroscope 106', and thus, the sampling position of the Raman spectroscopy excitation light on the target object is not affected.

In the second mode, when the mirror surfaces of the first flip mirror 301 and the second flip mirror 302 are not parallel to the light path between the first beam splitting mirror 102 and the second dichroscope 106', for example, they are arranged at angles shown in FIG. 2, the first flip mirror 301 is configured to receive and reflect light transmitted by the first beam splitting mirror 102, the first scanning galvanometer 303 is configured to receive and reflect reflected light from the first flip mirror 301, the second scanning galvanometer 304 is configured to receive and reflect reflected light from the first scanning galvanometer 303, the second flip mirror 302 is configured to receive and reflect reflected light from the second scanning galvanometer 304, the second dichroscope 106' is configured to receive reflected light from the second flip mirror, and the first coupling objective lens 103 is configured to receive emergent light from the second dichroscope 106'. The co-localization module 300 in the second mode will affect the Raman spectroscopy excitation light. For example, by rotating the first scanning galvanometer 303 and/or the second scanning galvanometer 304 around a preset axis, the emergent light from the first beam splitting mirror 102 will be deviated from a direction of an original light path (such as a direction of the light path in the first mode) at a certain angle, which leads to a change of a position of the incident light from the second dichroscope 106'. As a result, the sampling position of the Raman spectroscopy excitation light on the target object is changed. In the present implementation, the first scanning galvanometer 303 and the second scanning galvanometer 304 can respectively rotate along axes orthogonal to each other.

However, the present disclosure is not limited thereto, and spatial orientations of the axes for rotating the first scanning galvanometer 303 and the second scanning galvanometer 304 can be set by the skilled in the art on the basis of above disclosure according to an actual situation or as required. An axis with a certain orientation in a given coordinate system can be selected, and thus, a position/angle/shape of the Raman spectroscopy excitation light is affected in different modes by rotating the first scanning galvanometer 303 and the second scanning galvanometer 304. In this implementation, each of the first scanning galvanometer 303 and the second scanning galvanometer 304 adopts the MEMS-driven reflecting mirror. However, the present disclosure is not limited thereto, and other optical elements, such as the Galvo galvanometer, with the same function can be used by the skilled in the art on the basis of above disclosure according to an actual situation or as required.

The multi-modal imaging device according to another implementation involved in FIG. 5 in the accompanying drawings of the description of the present disclosure has a plurality of operating modes, one of which is only exemplarily listed hereinafter.

Figure 7A:
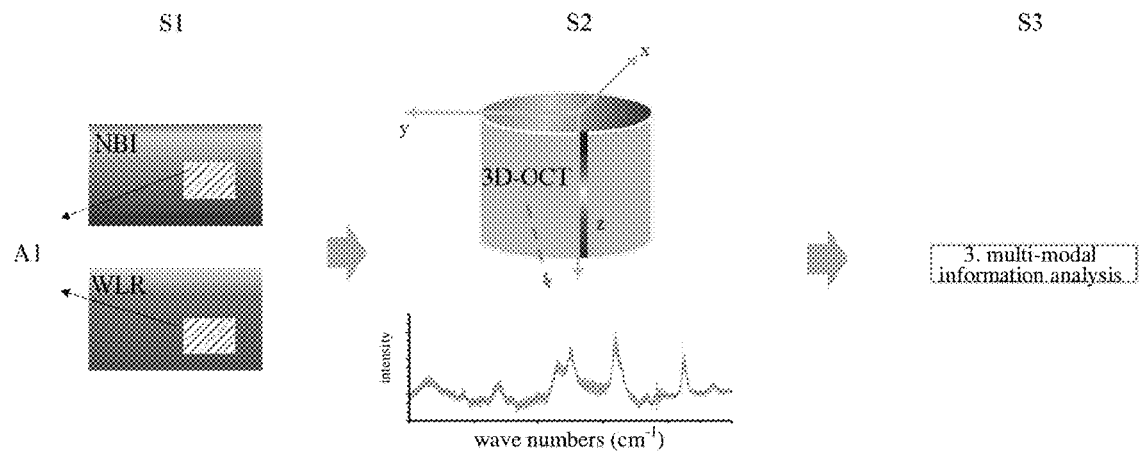
FIG. 7a shows a co-localization detection process actually generated during operation of a multi-modal imaging device according to another implementation of an embodiment of the present disclosure.

As one operating mode, a co-localization detection process thereof may refer to FIG. 7a. In this mode, by using the detection lens 502, sizes of light spots of the optical coherence tomography module 200 and the Raman spectroscopic analysis module 100 on the target object are smaller than the size of the concerned area. In step S1, the target object is imaged by NBI or WLR, and the concerned area A1 (a shadow part with slashes) is recognized. The recognition process can be performed by operating personnel or a doctor or by means of an algorithm. In a preferred implementation, the concerned area (a tumor or suspected tumor part) is automatically recognized by a deep learning model (CNN) image segmentation algorithm. In step S2, the remote scanning sub-module 205' controls the second sampling position of the optical coherence tomography module 200, thereby performing scanning and testing in the concerned area A1 to obtain the Raman spectroscopic information, it is basically synchronous and/or simultaneous that the co-localization module 300 controls the first sampling position of the Raman spectroscopic analysis module 100, thereby performing scanning and testing in the concerned area A1 to obtain the Raman spectroscopic information, and thus, the Raman spectroscopic information and the tissue structure image information which are spatially co-localized can be obtained; wherein the Raman spectroscopic information can reflect structural information, such as lipid and proteins, of specific molecules, and a signal intensity is related to a concentration; and therefore, the selection of the specific molecules related to the occurrence of cancer lesion is very beneficial to cancer screening and test. In step S3, the obtained multi-modal information which is spatially co-localized is analyzed. Preferably, analysis is performed by fusion by using the LSTM algorithm. Thus, it can be seen that the multi-modal imaging device in the present disclosure controls the first sampling position of the Raman spectroscopic analysis module 100 by using the co-localization module 300 to be scanned, analyzed/imaged with the second sampling position of the optical coherence tomography module 200 in the concerned area, which allows to obtain the Raman spectroscopic information and tissue structure image information which are spatially co-localized. Due to high spatial consistency, the multi-modal information of the same precise position in the true sense is obtained in the present disclosure, which is beneficial to improvement of the correlation between the Raman spectroscopic information and the tissue structure image information, thereby improving the accuracy and efficiency of diagnosis/screening.

Figure 7B:
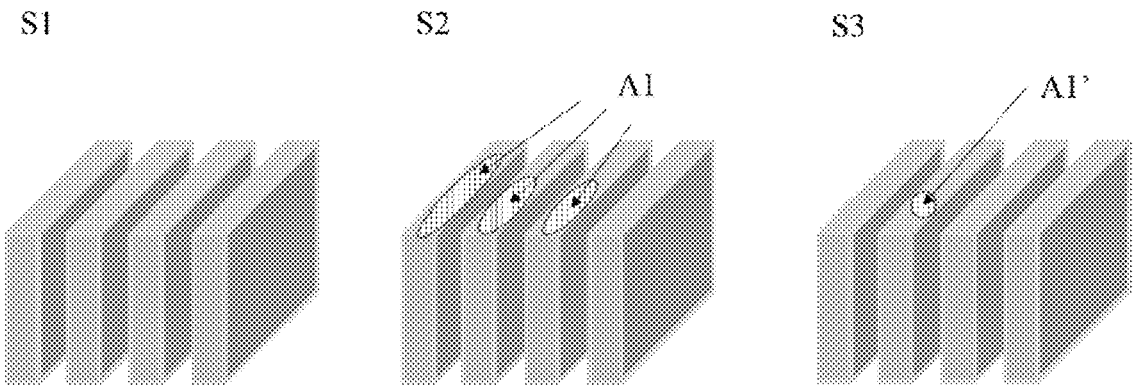
FIG. 7b shows another co-localization detection process actually generated during operation of a multi-modal imaging device according to another implementation of an embodiment of the present disclosure.

As another operating mode, a co-localization detection process thereof may refer to FIG. 7*b*. In step S1, a 3D-OCT image is obtained after line-by-line scanning performed by the MEMS-driven reflecting mirror of the remote scanning sub-module 205'. In step S2, the concerned area A1 (a shadow part with slashes) is recognized. The recognition process can be performed by operating personnel or a doctor or by means of an algorithm. In step S3, the sampling position A1' (a shadow part with slashes) of the Raman spectroscopic analysis module is controlled by the co-localization module 300, thereby obtaining the Raman spectroscopic information in the concerned area A1. The Raman spectroscopic information can reflect structural information, such as lipid and proteins, of specific molecules, and a signal intensity is related to a concentration. Therefore, the selection of the specific molecules related to the occurrence of cancer lesion is very beneficial to cancer screening and test. Optionally, the multi-modal information (OCT tissue structure image and co-localized Raman spectroscopy data) is fused by using the LSTM algorithm, which can further improve the accuracy of cancer diagnosis. Thus, it can be seen that the co-localization module 300 in the present disclosure achieves high-efficiency cooperative operation of Raman spectroscopic analysis and optical coherence tomography by controlling the sampling position of the Raman spectroscopy excitation light in the specific concerned area, so that high-accuracy and high-specificity screening and diagnosis for cancers/tumors can be achieved. As mentioned above, the present disclosure is not limited thereto, it is also possible that the concerned area A1 is obtained by using the Raman spectroscopic analysis module 100, and the second sampling position of the optical coherence tomography module 200 is controlled to detect the concerned area A1 so as to obtain the Raman spectroscopic information and the tissue structure image information which are spatially co-localized. Such a mode has the advantages that the concerned area can be obtained based on two-dimensional Raman spectroscopic information, and the corresponding axial tissue structure image information is further obtained by using 3D-OCT imaging. The skilled in the art can select a specific corresponding implementation on the basis of the above-mentioned disclosed contents according to different concerns.

In the multi-modal imaging device in the present disclosure, exemplary technical parameters of swept OCT and Raman are shown as follows:

the technical parameters of the OCT include: an imaging speed is 2-5 volume imaging/s or 200-500 B-scan frames/s, an imaging field of view is 0.5 mm to 2 mm, and a resolution and an imaging depth depend on a central wavelength of a light source; if the central wavelength is 1325 nm, the resolution is 15-20 µm, and the depth is 1-2 mm; and if the central wavelength is 800 nm, the resolution is 4-10 µm, and the depth is 0.5-1 mm.

The technical parameters of a Raman system include: a spectroscopic acquisition speed is 2-5 Hz, a spectroscopic resolution is 5-10 wave numbers, a range of a wavelength received by the spectrometer is 800-1100 nm, and a Raman spectroscopy detection range is 800-1800 wave numbers and 2800-3600 wave numbers.

It can be known from FIGS. 1 to 7 and the above-mentioned detailed description for the specific implementation in the embodiment of the present disclosure that the co-localization module of the multi-modal imaging device in the present disclosure is configured to control the first sampling position of the excitation light in the Raman spectroscopic analysis module and/or the second sampling position in the optical coherence tomography module according to the determined concerned area of the target object, so that the first sampling position and the second sampling position are spatially co-localized in the concerned area. That is to say, the multi-modal imaging device in the present disclosure controls the first sampling position of the Raman spectroscopic analysis module by using the co-localization module to be cooperated or matched with a spatial detection area for scanning imaging of the optical coherence tomography module (for example, the first sampling position basically overlaps with the concerned area, and then, the scanning imaging of the optical coherence tomography module is performed in the concerned area, or the first sampling position is controlled to be detected in the concerned area synchronously and/or simultaneously with the scanning imaging of the optical coherence tomography module, which allows to obtain the Raman spectroscopic information and tissue structure image information which are spatially co-localized. Due to high spatial consistency, the multi-modal information of the same precise position is obtained in the present disclosure, which is beneficial to improvement of the correlation between the Raman spectroscopic information and the tissue structure image information, thereby improving the accuracy and efficiency of diagnosis/screening.

Besides, in one operating mode, the optical coherence tomography module of the multi-modal imaging device in the present disclosure is configured to obtain the tissue structure image of the target object and determine the concerned area of the target object, and the co-localization module is configured to control the (first) sampling position of the excitation light in the Raman spectroscopic analysis module according to the determined concerned area, thereby obtaining Raman spectroscopic information of different positions in the concerned area. Obviously, in such an implementation, the Raman spectroscopic information and the tissue structure image which are spatially co-localized are also obtained. On the basis of obtaining the beneficial spatially co-localized information, such an implementation achieves cooperative operation of the two modules, as a result, the operating personnel are allowed to preliminarily affirm, according to the tissue structure image, the concerned area where a cancer risk is suspected, and next, the co-localization module guides and controls the sampling position of the Raman spectroscopy, thereby obtaining the Raman spectroscopic information of the concerned area, and obtaining more accurate information serving as a diagnosis basis according to the advantages of high accuracy and specificity of Raman spectroscopy. The concerned area can be determined according to an algorithm or experience of the operating personnel. In a preferred implementation, the concerned area is rapidly and automatically recognized according to the algorithm, and then, the co-localization module guides the Raman spectroscopy excitation light to the sampling position, thereby obtaining relatively accurate spectroscopic information of the specific molecules (such as lipid and proteins) related to cancers/tumors, which serves as a diagnosis basis; and in this implementation, the process from recognizing the concerned area to guiding the Raman spectroscopy excitation light through the co-localization module can be automated, which allows in-vivo real-time and precise cancer test. In above process, the co-localization module can reduce areas which need to be tested by Raman spectroscopic analysis, that is to say, it is unnecessary to perform Raman spectroscopic analysis on all areas, but only the concerned area is analyzed, which avoids the defect of low test speed of Raman spectroscopic analysis to a great extent, however, the advantages of high accuracy and specificity of Raman spectroscopic analysis are still utilized, so that the overall test efficiency is increased.

In addition, the co-localization module in the present disclosure is switchable between the two modes, so that a co-localization function is disenabled and enabled as required.

Besides, by disposing the probe of the multi-modal imaging device in the present disclosure, the size of the probe can be reduced, for example, the size of the probe can be reduced to 2-10 mm and even 2-5 mm, which is beneficial to integration into a working channel of an existing endoscope system, thereby being beneficial to clinical application.

Finally, with cervical cancer mentioned in the background art as an example, when the multi-modal imaging device in the present disclosure is used as an endoscope for diagnosis, expectably, it can be obtained in a cooperative, efficient, non-invasive and real-time mode that the sensitivity and the specificity of diagnosis for CIN are higher than 98%, and the accuracy of diagnosis for CIN1 early precancerous lesions is higher than 90%.

Besides, a control method for the operating device according to an implementation of the present disclosure may be recorded in a computer-readable recording medium. Specifically, according to the present disclosure, a computer-readable recording medium having a computer-executable instruction stored thereon can be provided, and the processor, when executing the computer-executable instruction, can perform the above-mentioned control method. Examples of the computer-readable recording medium may include a magnetic medium (such as a hard disk, a floppy disk, and a magnetic tape); an optical medium (such as a CD-ROM and a DVD); a magnetic-optical medium (such as a compact disc); and a particularly prepared hardware device (such as a read-only memory (ROM), a random access memory (RAM), and a flash memory) configured to store and execute program instructions. Besides, according to the present disclosure, equipment including a processor and a memory can be further provided. Computer-executable instructions are stored in the memory, wherein the processor, when executing the computer-executable instructions, performs the above-mentioned control method. Examples of the computer-executable instructions include machine codes generated by a compiler and files including advanced codes that can be executed by a computer by using an interpreter.

It should be noted that flow diagrams and block diagrams in the accompanying drawings illustrate possibly achieved system architectures, functions, and operations of systems, methods, and computer program products according to various implementations of the present disclosure. In view of this point, each box in the flow diagrams or block diagrams can represent a module, a program segment, or a part of the codes, and the module, the program segment, or a part of the codes includes at least one executable instruction for achieving a specified logical function. It should be also noted that, in some implementations as substitutions, functions marked in the box can also occur in a different order than that marked in the accompanying drawings. For example, two consecutively-represented boxes can be actually executed in parallel basically, and they can sometimes be executed in an opposite order, which depends on an involved function. It should be also noted that each box in the block diagrams and/or the flow diagrams and combinations of the boxes in the block diagrams and/or the flow diagrams can be achieved by using a special-purpose hardware-based system that performs specified functions or operations, or can be achieved by using a combination of special-purpose hardware and computer instructions.

Generally speaking, the various disclosed exemplary embodiments or implementations can be implemented in hardware or a special-purpose circuit, software, firmware, logic or any combinations thereof. Some aspects can be implemented in hardware, and other aspects can be implemented in firmware or software that can be executed by a controller, a microprocessor, or other computing equipment. When various aspects of the embodiment of the present disclosure are illustrated or described as block diagrams and flow diagrams, or represented by some other graphics, it is understood that the boxes, device, system, technology, or method described herein can be implemented as non-restrictive examples in hardware, software, firmware, a special-purpose circuit or logic, general-purpose hardware or a controller or other computing equipment, or some combinations thereof.

The exemplary implementations of the present disclosure described in detail above are only illustrative, rather than restrictive. It should be understood by those skilled in the art that various modifications and combinations can be performed on these embodiments or features thereof without departing from the principle and spirit of the present disclosure, and such modifications shall fall within the scope of the present disclosure.

What is claimed is:

1. A multi-modal imaging device, comprising:
   a Raman spectroscopic analysis module configured to obtain Raman spectroscopic information of a target object on a first sampling position by using excitation light;
   an optical coherence tomography module configured to obtain a tissue structure image of the target object on a second sampling position by using imaging detection light; and
   a co-localization module configured to control the first sampling position of the excitation light in the Raman spectroscopic analysis module according to a determined concerned area of the target object, so that the first sampling position and the second sampling position are spatially co-localized in the determined concerned area;
   an image processing module configured to fuse the Raman spectroscopic information of the first sampling position and the tissue structure image of the second sampling position, which are spatially co-localized, so as to generate fused multi-modal information of the determined concerned area;

wherein spatial co-localization means that the Raman spectroscopic information from the Raman spectroscopic analysis module and tissue structure image information from the optical coherence tomography module are from a same spatial position, wherein the co-localization module is arranged in an incident light path of the excitation light from the Raman spectroscopic analysis module, wherein the multi-modal imaging device comprises a probe provided with a shell and a detection window and configured to detect the target object, and the excitation light from the Raman spectroscopic analysis module and the imaging detection light from the optical coherence tomography module are coupled in the probe, wherein the Raman spectroscopic analysis module comprises a first light source, a first beam splitting mirror, a first coupling objective lens, a first optical fiber, a spectrometer, a first lens group, and a first dichroscope; and the first beam splitting mirror is configured to transmit excitation light from the first light source and reflect Raman spectroscopy scattering signal light from the target object, the spectrometer is configured to receive the Raman spectroscopy scattering signal light from the target object reflected by the first beam splitting mirror, the first coupling objective lens is configured to receive emergent light from the co-localization module, the first optical fiber is configured to receive emergent light from the first coupling objective lens, the first lens group is configured to receive emergent light from the first optical fiber, and the first dichroscope is configured to receive and transmit emergent light from the first lens group, wherein the first lens group comprises a collective lens.

2. The multi-modal imaging device according to claim 1, wherein a grating and a receiving lens are arranged between the spectrometer and the first beam splitting mirror, the grating is configured to split reflected light from the first beam splitting mirror, the receiving lens is configured to receive emergent light from the grating, and the spectrometer is configured to receive emergent light from the receiving lens.

3. The multi-modal imaging device according to claim 1, wherein the first optical fiber comprises a multi-core optical fiber, wherein a central fiber core group consisting of at least one fiber core of a central part of the multi-core optical fiber is configured to transmit Raman spectroscopy excitation light from the first light source, and a plurality of peripheral fiber core groups of groups consisting of at least one fiber core surrounding the central part in the multi-core optical fiber are configured to transmit the Raman spectroscopy scattering signal light, wherein a band-pass fiber is arranged on a tail end of a side, close to the target object, of the central fiber core group, and at least one of notch fibers or long-pass filters are arranged on tail ends of sides, close to the target object, of the peripheral fiber core groups.

4. The multi-modal imaging device according to claim 1, wherein the optical coherence tomography module comprises a second light source, a beam splitter, an interferometer, a second optical fiber, a scanning sub-module, a detector, a second lens group, and a reflecting mirror;

the second light source, the interferometer, the detector and the scanning sub-module are optically coupled to the beam splitter; the scanning sub-module is optically coupled to the beam splitter via the second optical fiber; and one part of the second optical fiber passes through the scanning sub-module;

the second lens group is configured to receive emergent light from the second optical fiber, the reflecting mirror is configured to reflect emergent light from the second lens group, and the first dichroscope is configured to reflect reflected light from the reflecting mirror, so that light from the first lens group is coupled with light from the second lens group, wherein at least one of the second light source, the interferometer or the detector are optically coupled to the beam splitter via a coupling optical fiber.

5. The multi-modal imaging device according to claim 4, wherein the first lens group and the second lens group are arranged in parallel in the probe, and the first dichroscope, the scanning sub-module, the reflecting mirror and at least one part of the second optical fiber are arranged in the probe, wherein the scanning sub-module is configured to control imaging detection light from the second light source by controlling a position of the second optical fiber so as to obtain a position of the tissue structure image of the target object, wherein the scanning sub-module comprises a piezoelectric ceramic tube, wherein the second lens group comprises a second focusing lens and a diffraction lens, and the diffraction lens is arranged between the second focusing lens and the reflecting mirror, wherein a circulator is arranged between the detector and the beam splitter.

6. The multi-modal imaging device according to claim 4, wherein the co-localization module is arranged in an incident light path of the excitation light from the Raman spectroscopic analysis module, wherein the co-localization module is arranged between the first beam splitting mirror and the first coupling objective lens, wherein the co-localization module has a first mode and a second mode which are switchable;

in the first mode, the co-localization module does not change the first sampling position; and in the second mode, the co-localization module is configured to control the first sampling position.

7. The multi-modal imaging device according to claim 6, wherein the co-localization module comprises a first flip mirror, a second flip mirror, a first scanning galvanometer, and a second scanning galvanometer; the first flip mirror and the second flip mirror are arranged between the first beam splitting mirror and the first coupling objective lens;

the first flip mirror and the second flip mirror are configured to control mirror surfaces of the first flip mirror and the second flip mirror to be parallel or not parallel to a light path between the first beam splitting mirror and the first coupling objective lens by rotating around an axis orthogonal to the light path between the first beam splitting mirror and the first coupling objective lens; and the first scanning galvanometer and the second scanning galvanometer are configured to control the first sampling position by rotating around different axes;

wherein in the first mode, the mirror surfaces of the first flip mirror and the second flip mirror are parallel to the light path between the first beam splitting mirror and the first coupling objective lens; and in the second mode, the mirror surfaces of the first flip mirror and the second flip mirror are not parallel to the light path between the first beam splitting mirror and the first coupling objective lens.

8. The multi-modal imaging device according to claim 7, wherein in the second mode, the first flip mirror is configured to receive and reflect light transmitted by the first beam splitting mirror, the first scanning galvanometer is configured to receive and reflect reflected light from the first flip mirror, the second scanning galvanometer is configured to receive and reflect reflected light from the first scanning galvanometer, the second flip mirror is configured to receive and reflect reflected light from the second scanning galvanometer, and the first coupling objective lens is configured to receive reflected light from the second flip mirror.

9. The multi-modal imaging device according to claim 1, further comprising a detection lens and a detection optical fiber;
the Raman spectroscopic analysis module further comprises a second dichroscope;
the optical coherence tomography module comprises a second light source, a beam splitter, an interferometer, a remote scanning sub-module, and a detector;
wherein the first beam splitting mirror, the co-localization module, the second dichroscope and the first coupling objective lens are sequentially arranged in a transmission direction of emergent light from the first light source;
the second dichroscope is configured to transmit emergent light from the co-localization module or emergent light from the first beam splitting mirror and reflect the imaging detection light from the second light source, to couple the emergent light with the imaging detection light;
the first coupling objective lens is configured to receive coupled light from the second dichroscope;
the detection optical fiber is configured to receive emergent light from the first coupling objective lens;
the detection lens is configured to receive emergent light from the detection optical fiber;
the remote scanning sub-module is arranged between the second dichroscope and the beam splitter, is configured to receive and reflect the imaging detection light from the second light source and transmitted by the beam splitter, and is configured to control the imaging detection light from the second light source by rotating around at least two axes so as to obtain a position of the tissue structure image of the target object; and
the second light source, the interferometer and the detector are optically coupled to the beam splitter.

10. The multi-modal imaging device according to claim 9, wherein at least one of the second light source, the interferometer, or the detector are optically coupled to the beam splitter by a coupling optical fiber,
wherein the multi-modal imaging device comprises a probe, and the detection lens and at least one part of the detection optical fiber are arranged in the probe,
wherein the co-localization module has a first mode and a second mode which are switchable;
in the first mode, the co-localization module does not change the first sampling position; and
in the second mode, the co-localization module is configured to control the first sampling position.

11. The multi-modal imaging device according to claim 10, wherein the co-localization module comprises a first flip mirror, a second flip mirror, a first scanning galvanometer, and a second scanning galvanometer; the first flip mirror and the second flip mirror are arranged between the first beam splitting mirror and the second dichroscope;
the first flip mirror and the second flip mirror are configured to control mirror surfaces of the first flip mirror and the second flip mirror to be parallel or not parallel to a light path between the first beam splitting mirror and the second dichroscope by rotating around an axis orthogonal to the light path between the first beam splitting mirror and the second dichroscope; and the first scanning galvanometer and the second scanning galvanometer are configured to control the first sampling position by rotating around different axes;
wherein in the first mode, the mirror surfaces of the first flip mirror and the second flip mirror are parallel to the light path between the first beam splitting mirror and the second dichroscope; and
in the second mode, the mirror surfaces of the first flip mirror and the second flip mirror are not parallel to the light path between the first beam splitting mirror and the second dichroscope.

12. The multi-modal imaging device according to claim 11, wherein in the second mode, the first flip mirror is configured to receive and reflect light transmitted by the first beam splitting mirror, the first scanning galvanometer is configured to receive and reflect reflected light from the first flip mirror, the second scanning galvanometer is configured to receive and reflect reflected light from the first scanning galvanometer, the second flip mirror is configured to receive and reflect reflected light from the second scanning galvanometer, and the second dichroscope is configured to receive and transmit reflected light from the second flip mirror.

13. The multi-modal imaging device according to claim 10, wherein the detection optical fiber comprises a multi-core optical fiber,
a central fiber core group consisting of at least one fiber core of a central part of the multi-core optical fiber is configured to transmit the imaging detection light from the second light source and light from the target object and configured to obtain the tissue structure image of the target object,
a plurality of peripheral fiber core groups of groups consisting of at least one fiber core surrounding the central part in the multi-core optical fiber are respectively configured to transmit Raman spectroscopy excitation light and Raman spectroscopy scattering signal light from the first light source,
wherein the peripheral fiber core groups configured to transmit the Raman spectroscopy excitation light and the peripheral fiber core groups configured to transmit the Raman spectroscopy scattering signal light are arranged alternatively.

14. The multi-modal imaging device according to claim 13, wherein band-pass fibers are arranged on tail ends of sides, close to the target object, of the central fiber core group and the peripheral fiber core groups configured to transmit the Raman spectroscopy excitation light, and at least one of notch fibers or long-pass filters are arranged on tail ends of sides, close to the target object, of the peripheral fiber core groups configured to transmit the Raman spectroscopy scattering signal light,
wherein a cross sectional area of the central fiber core group is greater than a cross sectional area of single peripheral fiber core group configured to transmit the Raman spectroscopy excitation light and the cross sectional area of single peripheral fiber core group configured to transmit the Raman spectroscopy scattering signal light.

15. The multi-modal imaging device according to claim 10, wherein a grating and a receiving lens are arranged between the spectrometer and the first beam splitting mirror, the grating is configured to split reflected light from the first beam splitting mirror, the receiving lens is configured to receive emergent light from the grating, and the spectrometer is configured to receive emergent light from the receiving lens.

16. The multi-modal imaging device according to claim 9, wherein the first light source and the second light source are respectively provided with a first light source switch and a second light source switch, and an optional middle reflecting mirror configured to reflect the excitation light from the first light source to the first beam splitting mirror is arranged between the first light source and the first beam splitting mirror.

17. The multi-modal imaging device according to claim 1, wherein the co-localization module is configured to move the first sampling position to overlap with a position of the determined concerned area.

18. The multi-modal imaging device according to claim 1, wherein the first lens group is configured to enable a size of a light spot of the excitation light from the Raman spectroscopic analysis module on the first sampling position to be is a same as a size of the determined concerned area, wherein the co-localization module is configured to move the first sampling position to a position overlapping with the determined concerned area.

19. The multi-modal imaging device according to claim 9, wherein the co-localization module is configured to synchronously control the first sampling position and the second sampling position with the remote scanning sub-module, so that the first sampling position overlaps with the second sampling position.

20. The multi-modal imaging device according to claim 1, wherein the determined concerned area of the target object is determined from the tissue structure image of the target object, which is acquired by an imaging device different from the multi-modal imaging device, the Raman spectroscopic information acquired by the Raman spectroscopic analysis module or the tissue structure image acquired by the optical coherence tomography module.

* * * * *